(12) United States Patent
Palczewski et al.

(10) Patent No.: US 8,889,660 B2
(45) Date of Patent: *Nov. 18, 2014

(54) METHODS FOR TREATING OBESITY OR AN OBESITY RELATED CONDITION

(71) Applicant: Case Western Reserve University, Cleveland, OH (US)

(72) Inventors: Krzysztof Palczewski, Bay Village, OH (US); Radu Moise, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,592

(22) Filed: Nov. 16, 2012

(65) Prior Publication Data

US 2013/0072555 A1    Mar. 21, 2013

Related U.S. Application Data

(63) Continuation of application No. 12/445,100, filed on Jan. 20, 2010, now Pat. No. 8,338,394.

(51) Int. Cl.
| | | |
|---|---|---|
| *A61K 31/59* | (2006.01) | |
| *A61K 31/203* | (2006.01) | |
| *A61K 31/07* | (2006.01) | |
| *A61K 31/215* | (2006.01) | |

(52) U.S. Cl.
CPC ............... *A61K 31/07* (2013.01); *A61K 31/203* (2013.01); *A61K 31/215* (2013.01); *Y10S 514/909* (2013.01)
USPC .......................................... 514/168; 514/909

(58) Field of Classification Search
CPC ............................ A61K 31/07; A61K 31/203
USPC ................................................. 514/168, 909
See application file for complete search history.

(56) References Cited

U.S. PATENT DOCUMENTS

| | | | |
|---|---|---|---|
| 4,544,550 A | 10/1985 | Rodolfo | |
| 6,437,003 B1 | 8/2002 | Roullet et al. | |
| 8,338,394 B2 * | 12/2012 | Palczewski et al. | 514/168 |
| 2006/0252107 A1 | 11/2006 | Kubota et al. | |
| 2006/0281821 A1 | 12/2006 | Palczewski et al. | |
| 2008/0214668 A1 | 9/2008 | Roullet et al. | |
| 2008/0221208 A1 | 9/2008 | Palczewski et al. | |
| 2008/0249042 A1 | 10/2008 | Moise et al. | |
| 2008/0275134 A1 | 11/2008 | Palczewski et al. | |

FOREIGN PATENT DOCUMENTS

CN          1444932 A   * 10/2003

OTHER PUBLICATIONS

English abstract and claims of CN 1444932 A (2003).*
Textbook of Biochemistry With Clinical Correlations 1078-79 (Thomas M. Devlin ed., 2006).
Lippincott's Illustrated Reviews, Biochemistry, 3d ed. 351 (Champe et al. eds. 2005).
Moise, Alexander R. et al., "Identification of All-Trans-Retinol:All-Trans-13,14-Dihydroretinol Sturase", The Journal of Biological Chemistry, vol. 279, No. 48, Issue of Nov. 26, pp. 50230-50242, 2004.
Rewers, Marian, et al., "Insulin Sensitivity, Insulinemia, and Coronary Artery Disease", Diabetes Care, vol. 27, No. 3, Mar. 2004.
Mosie, Alexander, R., et al., "Metabolism and Transaction Activity of 13,14-Dihydroretinoic Acid", The Journal of Biological Chemistry, vol. 280, No. 30, Issue of Jul. 29, pp. 27815-27835, 2005.

* cited by examiner

*Primary Examiner* — Kevin E Weddington
(74) *Attorney, Agent, or Firm* — Tarolli, Sundheim, Covell & Tummino LLP

(57) ABSTRACT

In one aspect of the present invention, a pharmaceutical composition for treating a metabolic disease in a mammalian subject includes a therapeutically effective amount of (R)-all-trans-13,14-dihydroretinol and a pharmaceutically acceptable carrier or diluent. In another aspect of the present invention, pharmaceutical composition for treating a metabolic disease in a mammalian subject includes a therapeutically effective amount of (S)-all-trans-13,14-dihydroretinol and a pharmaceutically acceptable carrier or diluent. In a further aspect of the present invention, a method is provided for treating a metabolic disease in a mammalian subject. The method includes administering to the subject a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative in the subject.

7 Claims, 11 Drawing Sheets

Enantiomeric State of All-*trans*-13,14-dihydroretinol (13*R*)-all-trans-13,14-dihydroretinol (13*S*)-all-trans-13,14-dihydroretinol

METHODS FOR TREATING OBESITY OR AN OBESITY RELATED CONDITION

RELATED APPLICATION

This application is a Continuation of U.S. patent application Ser. No. 12/445,100, filed Jan. 20, 2010, which is a National Phase filing of PCT/US2007/080810, filed Oct. 9, 2007, which claims priority from U.S. Provisional Application No. 60/851,221, filed Oct. 12, 2006, the subject matter of which are incorporated herein by reference in their entirety.

GOVERNMENT FUNDING

This invention was made with government support under Grant No. R03EY015399 awarded by the National Institutes of Health, Eye Institute. The government has certain rights in the invention.

TECHNICAL FIELD

The present invention generally relates to compositions and methods for treating metabolic diseases, and more particularly to compositions and methods for treating metabolic diseases by modulating the level and/or activity of all-trans-retinol:all-trans-13,14-dihydroretinol saturase and enzymatic products thereof.

BACKGROUND OF THE INVENTION

Normal insulin production and regulation of blood glucose is a critical aspect of proper homeostasis. In humans, insulin is synthesized in the β cells of the islets of Langerhans in the pancreas, and is generally responsible for regulating carbohydrate metabolism. Specific cellular effects of insulin include increased fatty acid synthesis, decreased lipolysis, and increased glycogen synthesis. Defects in insulin production may result in various metabolic diseases, such as type 1 diabetes, in which insulin production is acutely impaired as a result of autoimmune pancreatic β cell destruction.

The regulation of blood glucose levels by insulin is achieved mainly by increased glucose transport into adipose and skeletal muscle tissue. The mechanism of glucose transport activation by insulin is the hormone-dependent enhancement of GLUT4 translocation from intracellular storage vesicles to the plasma membrane. Glucose uptake is increased proportionally to the increment of GLUT4 molecules in the plasma membrane. Insulin-responsive glucose transport is essential to the normal functioning and metabolism of fat and muscle tissue in normal human subjects. Insulin resistance of, for example, skeletal muscle glucose transport is a key defect in the development of metabolic diseases such as impaired glucose tolerance and type 2 diabetes.

A more detailed understanding of the molecular mechanisms responsible for insulin production and insulin-responsive glucose transport would greatly facilitate the development of therapeutic strategies aimed at modulating various metabolic diseases. In particular, the intracellular pathways and their respective molecules involved in such metabolic diseases serve as useful targets for treating metabolic diseases.

SUMMARY OF THE INVENTION

The present invention generally relates to compositions and methods for treating metabolic diseases, and more particularly to compositions and methods for treating metabolic diseases by modulating the level and/or activity of all-trans-retinol:all-trans-13,14-dihydroretinol saturase and enzymatic products thereof.

In one aspect of the present invention, a pharmaceutical composition for treating a metabolic disease in a mammalian subject comprises a therapeutically effective amount of all-trans-13,14-dihydroretinoid or all-trans-13,14-dihydroretinoid derivative and a pharmaceutically acceptable carrier or diluent.

In a further aspect, the all-trans-13,14-dihydroretinoid or all-trans-13,14-dihydroretinoid derivative comprises at least about 75%, 80%, 90%, 95%, or 99% (R)— all-trans-13,14-dihydroretinoid or (R)-all-trans-13,14-dihydroretinoid derivative. In one example, the (R)-all-trans-13,14-dihydroretinoid or (R)-all-trans-13,14-dihydroretinoid derivative can include at least about 75%, 80%, 90%, 95%, or 99% (R)-all-trans-13,14-dihydroretinol. In another aspect, the (R)-all-trans-13,14-dihydroretinoid or (R)-all-trans-13,14-dihydroretinoid derivative consists essentially of (R)-all-trans-13,14-dihydroretinol.

In yet a further aspect, the all-trans-13,14-dihydroretinoid or all-trans-13,14-dihydroretinoid derivative comprises at least about 75%, 80%, 90%, 95%, or 99% (S)— all-trans-13,14-dihydroretinoid or (S)-all-trans-13,14-dihydroretinoid derivative. In one example, the (S)-all-trans-13,14-dihydroretinoid or (S)-all-trans-13,14-dihydroretinoid derivative can include at least about 75%, 80%, 90%, 95%, or 99% (S)-all-trans-13,14-dihydroretinol. In another aspect, the (S)-all-trans-13,14-dihydroretinoid or (R)-all-trans-13,14-dihydroretinoid derivative consists essentially of (S)-all-trans-13,14-dihydroretinol.

In another aspect of the present invention, a method is provided for treating a metabolic disease in a mammalian subject. The method comprises administering to the subject a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative in the subject.

In another aspect of the present invention, a method is provided for treating obesity or an obesity-related condition in a mammalian subject. The method comprises administering to the subject a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative in the subject.

In another aspect of the present invention, a method is provided for increasing insulin production in a mammalian subject. The method comprises administering to the subject a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative in the subject.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1A is a histogram showing calcium responses of G-protein-coupled receptor 40 and Gα16 cells to 100 μM fatty acids and retinoic acids. FIG. 2A is a histogram showing calcium responses to retinoic acid compounds at 10 µM;

DETAILED DESCRIPTION

Figure 1A:
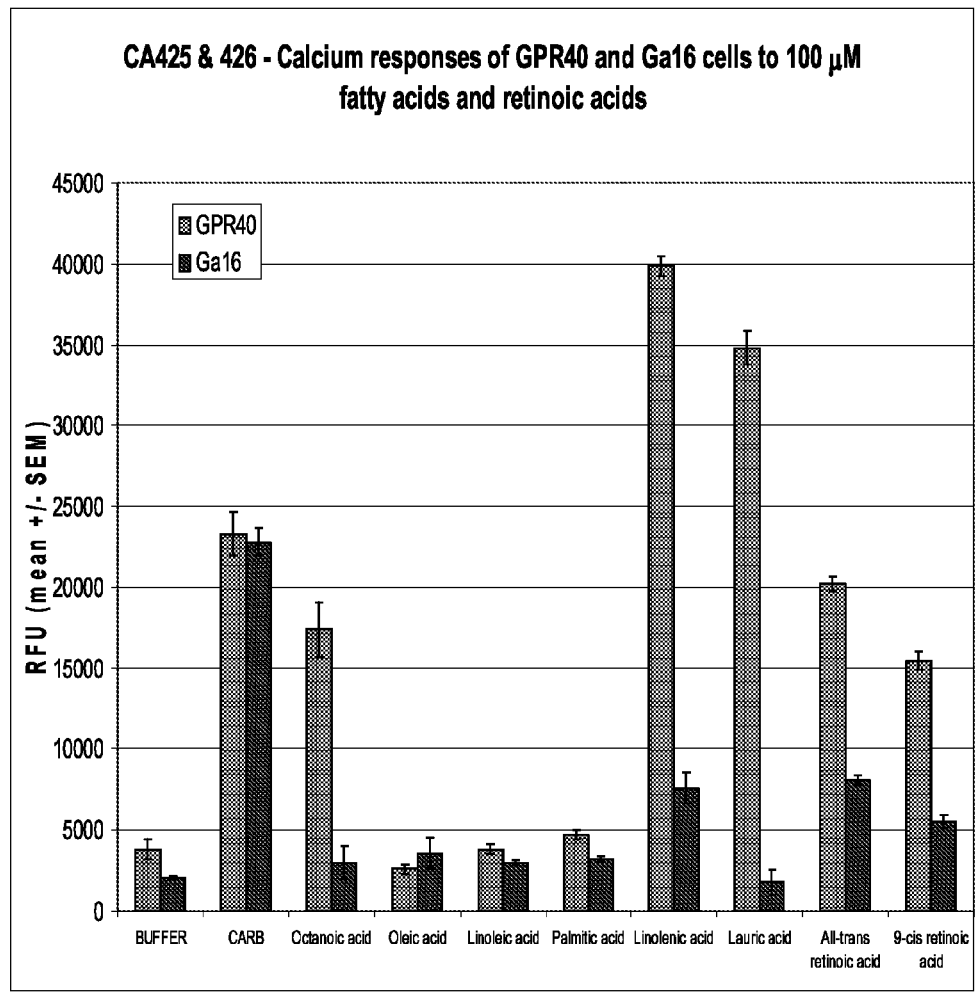
FIGS. 1A-B are a series of histographs showing the screening of potential receptors for all-trans-13,14-dihydroretinoic acid.
Figure 1B:
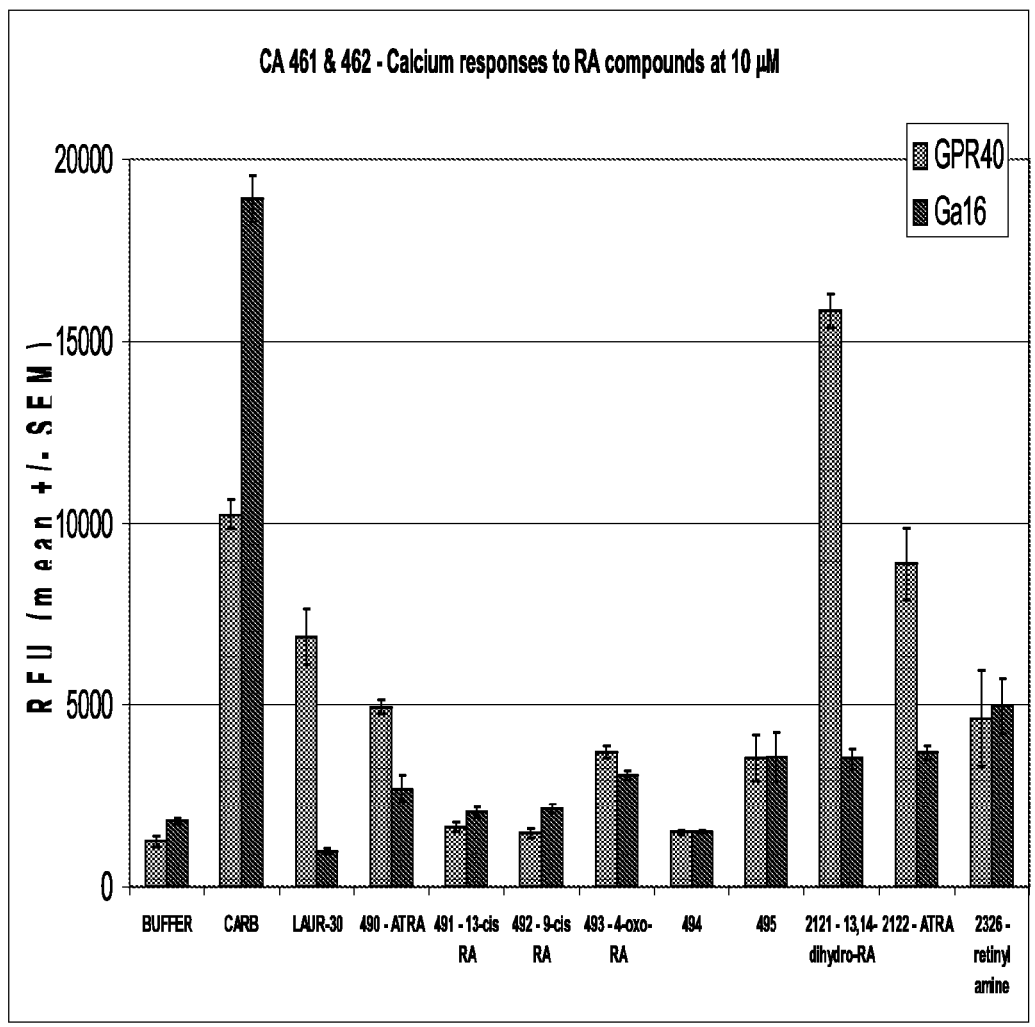
Figure 2:
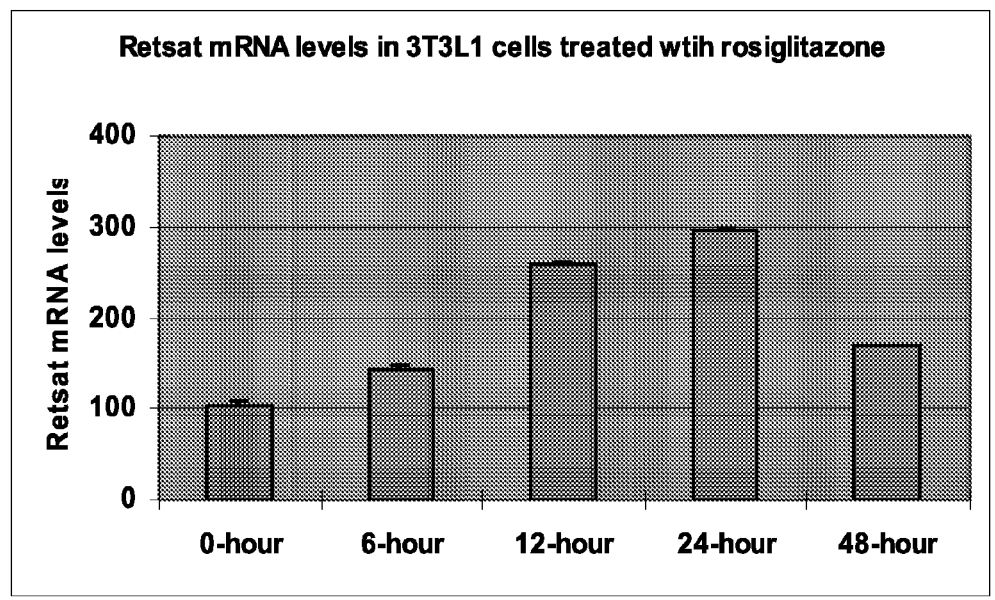
FIG. 2 is a histogram showing all-trans-retinol:all-trans-13,14-dihydroretinol saturase mRNA levels during NIH-3T3-L1 adipocyte differentiation.
Figure 3:
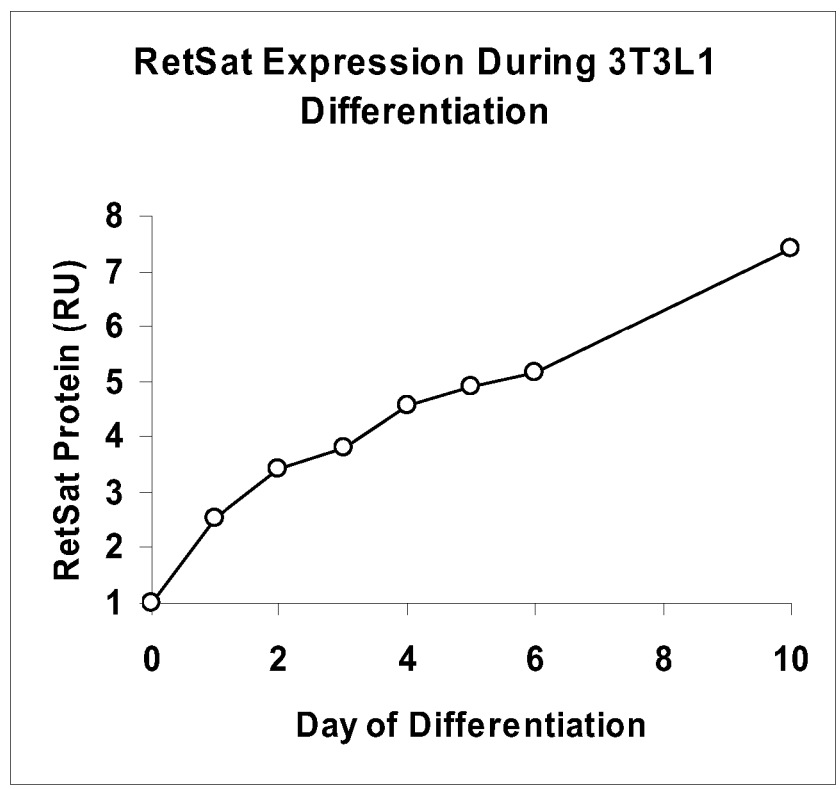
FIG. 3 is a graph showing all-trans-retinol:all-trans-13,14-dihydroretinol saturase expression during NIH-3T3-L1 adipocyte differentiation.
Figure 4:
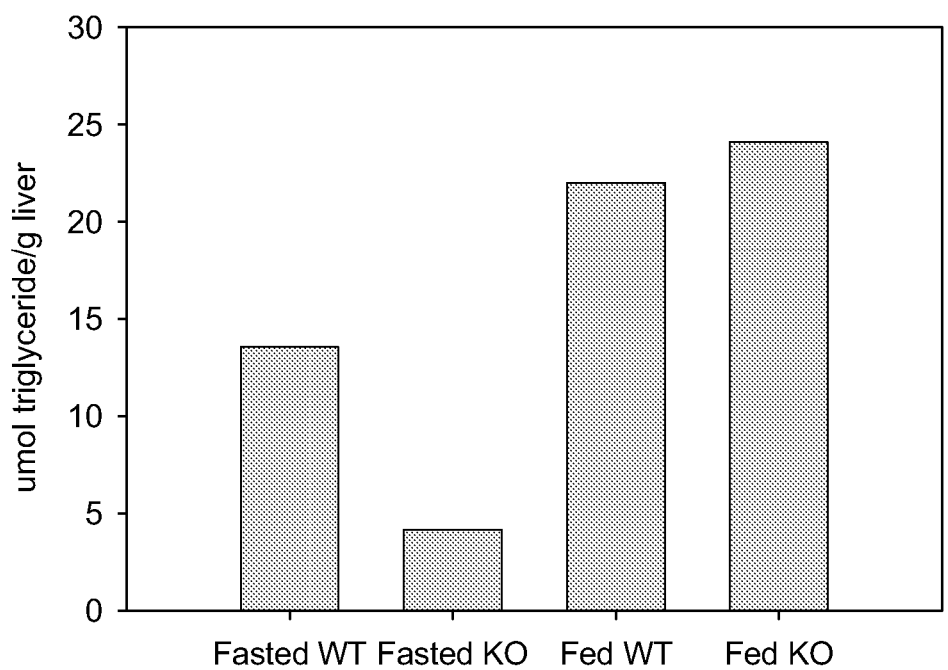
FIG. 4 is a histogram showing triglyceride levels in all-trans-retinol:all-trans-13,14-dihydroretinol saturase –/– mice during fasting.
Figure 5A:
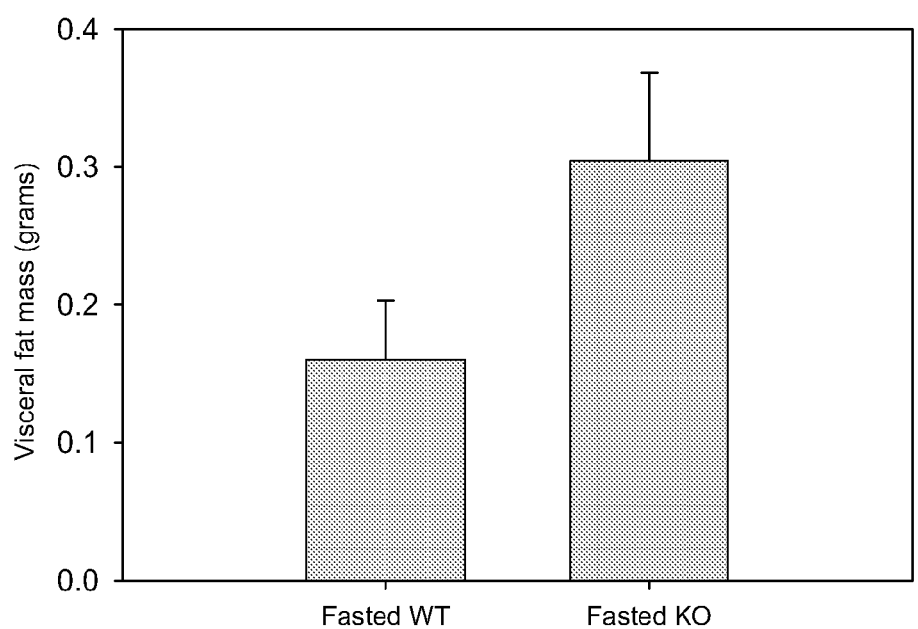
FIG. 5A is a histogram showing visceral fat mass in all-trans-retinol:all-trans-13,14-dihydroretinol saturase –/– mice during fasting.
Figure 5B:
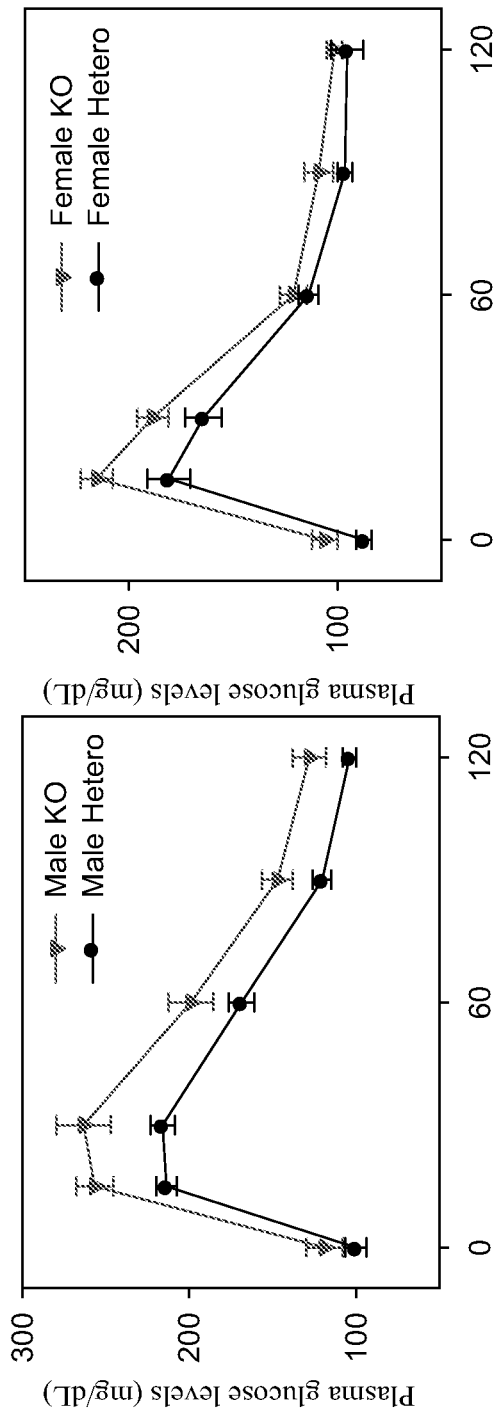
FIG. 5 B is a graph depicting the results of a glucose tolerance test in heterozygous all-trans-13,14-dihydroretinol saturase +/– mice and homozygous all-trans-13,14-dihydroretinol saturase –/– mice showing that all-trans-13,14-dihydroretinol saturase –/– mice have an impaired glucose response.

The present invention generally relates to compositions and methods of treating metabolic diseases, and more particularly to compositions and methods of treating metabolic diseases by modulating the level and/or activity of all-trans-retinol:all-trans-13,14-dihydroretinol saturase and enzymatic products thereof. The present invention is based on the discovery that all-trans-retinol:all-trans-13,14-dihydroretinol saturase –/– mice have impaired glucose tolerance response (FIG. 5 B) and an abnormal fasting response manifested by, visceral fat retention (FIG. 5 A), and low hepatic triglyceride levels (FIG. 4). The present invention is additionally based on the discovery that all-trans-retinol:all-trans-13,14-dihydroretinol saturase expression increases during adipocyte differentiation and is maintained in the mature adipocyte (FIGS. 2 and 3). Further, the present invention is based on the discovery that all-trans-13,14-dihydroretinoic acid, a downstream metabolite of all-trans-13,14-dihydroretinol, is an activator of the retinoic acid receptor and G-coupled-protein receptor 40 (GPR40) (FIGS. 1A-B). Based on these discoveries, the present invention provides methods for treating and diagnosing metabolic diseases such as obesity, impaired glucose tolerance, and diabetes.

It should be understood that the present invention is not limited to particular methods, reagents, compounds, compositions or biological systems, which can, of course, vary. It should also be understood that the terminology used herein is for the purpose of describing particular aspects of the present invention only, and is not intended to be limiting. Unless defined otherwise, all technical and scientific terms used herein have the same meaning as commonly understood by one of ordinary skill in the art to which the present invention pertains. Although any methods and materials similar or equivalent to those described herein can be used in the practice of the present invention, the preferred materials and methods are described herein. In describing and claiming the present invention, the following terminology will be used.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "polynucleotide" and "nucleic acid" refer to a polymer composed of a multiplicity of nucleotide units (ribonucleotide or deoxyribonucleotide or related structural variants) linked via phosphodiester bonds. A polynucleotide or nucleic acid can be of any length, but typically from about 6 nucleotides to about 100 nucleotides or larger. Polynucleotides and nucleic acids include RNA (e.g., mRNA), cDNA, genomic DNA, synthetic forms, mixed polymers, and both sense and antisense strands. Polynucleotides and nucleic acids can also be chemically or biochemically modified, or can contain non-natural or derivatized nucleotide bases. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Synthetic molecules that mimic polynucleotides in their ability to bind to a designated sequence via hydrogen bonding and other chemical interactions may also be included. Such molecules are known in the art and include, for example, those in which peptide linkages substitute for phosphate linkages in the backbone of the molecule.

The term "polypeptide" refers to a polymer of amino acids and its equivalent and does not refer to a specific length of the product; thus, peptides, oligopeptides and proteins are included within the definition of a polypeptide. A "fragment" refers to a portion of a polypeptide typically having at least 10 contiguous amino acids, more typically at least 20, and still more typically at least 50 contiguous amino acids of the polypeptide. A "derivative" is a polypeptide having conservative amino acid substitutions, as compared with another sequence. Derivatives further include, for example, glycosylations, acetylations, phosphorylations, and the like. An analog of a polypeptide can be, for example, a polypeptide containing one or more analogs of an amino acid (e.g., unnatural amino acids, and the like), polypeptides with substituted linkages, as well as other modifications known in the art, both naturally and non-naturally occurring.

The term "therapeutically effective amount" refers to an amount of a molecule (e.g., an all-trans-retinol:all-trans-13,14-dihydroretinol saturase polypeptide, an all-trans-retinol:all-trans-13,14-dihydroretinol saturase polynucleotide, an all-trans-13,14-dihydroretinoid, an all-trans-13,14-dihydroretinoid derivative, all-trans-13,14-dihydroretinoic acid, and/or all-trans-13,14-dihydroretinol) that is sufficient to modulate the level and/or activity of all-trans-retinol:all-trans-13,14-dihydroretinol saturase in at least one cell of a subject.

The term "sample" generally indicates a specimen of tissue, cells, plasma, serum, spinal fluid, lymph fluid, the external sections of the skin, respiratory, intestinal, and genitourinary tracts, tears, saliva, blood cells, hair, tumors, organs, other material of biological origin that contains polynucleotides, or in vitro cell culture constituents of any of these. A sample can further be in a semi-purified or purified form. A sample can be isolated from a mammal, such as a human, an animal, or any other organism expressing all-trans-retinol:all-trans-13,14-dihydroretinol saturase and/or a polynucleotide encoding all-trans-retinol:all-trans-13,14-dihydroretinol saturase.

The term "condition" refers to a disease or disorder associated with the level and/or activity of all-trans-retinol:all-trans-13,14-dihydroretinol saturase.

The term "metabolic disease" refers to a group of identified disorders in which errors of metabolism, imbalances in metabolism, or sub-optimal metabolism occur. The metabolic diseases as described herein also include diseases that can be treated through the modulation of metabolism, although the disease itself may or may not be caused by a specific metabolic defect. Such metabolic diseases may involve, for example, glucose and fatty acid oxidation pathways.

The term "obesity" as used herein is defined in the WHO classifications of weight. Underweight is less than 18.5 BMI (thin); healthy is 18.5-24.9 BMI (normal); grade 1 overweight is 25.0-29.9 BMI (overweight); grade 2 overweight is 30.0-39.0 BMI (obesity); grade 3 overweight is greater than or equal to 40.0 BMI. BMI is body mass index (morbid obesity) and is $kg/m^2$. Waist circumference can also be used to indicate a risk of metabolic complications. Waist circumference can be measured (in cm) at midpoint between the lower border of ribs and the upper border of the pelvis. Other measures of obesity include, but are not limited to, skinfold thickness and bioimpedance, which is based on the principle that lean mass conducts current better than fat mass because it is primarily an electrolyte solution.

The term "obesity-related condition" refers to any disease or condition that is caused by or associated with (e.g., by biochemical or molecular association) obesity or that is caused by or associated with weight gain and/or related biological processes that precede clinical obesity. Examples of obesity-related conditions include, but are not limited to, diabetes (e.g., type 1 diabetes, type 2 diabetes, and gestational diabetes), Syndrome X, hyperglycemia, hyperinsulinemia, impaired glucose tolerance, impaired fasting glucose, dyslipidemia, hypertriglyceridemia, insulin resistance, hypercholesterolemia, atherosclerosis, coronary artery disease, peripheral vascular disease, and hypertension.

The term "subject" refers to a mammal, such as a human being. As also used herein, the term "subject" may refer to a patient.

The term "pharmaceutical composition" refers to a preparation of one or more of the agents described herein with other chemical components such as physiologically suitable carriers and excipients. The purpose of a pharmaceutical composition is to facilitate administration of an agent to a subject.

As used herein, the "level" of all-trans-retinol:all-trans-13,14-dihydroretinol saturase refers to the concentration of all-trans-retinol:all-trans-13,14-dihydroretinol saturase in a medium.

As used herein, the "activity" of all-trans-retinol:all-trans-13,14-dihydroretinol saturase refers to the specific activity of all-trans-retinol:all-trans-13,14-dihydroretinol saturase. Specific activity is typically defined in terms of enzyme units per mg enzyme protein. An enzyme unit may be the amount of substrate converted to product per unit time under specific reaction conditions for pH and temperature. For example, an enzyme unit may be defined as that which catalyzes the transformation of 1 micromole of substrate per minute at 30° C. in an optimal chemical environment (e.g., pH and substrate concentration).

The term "modulate" as used herein refers to affecting a change in the level, activity, amount or other characteristic of a desired target, such as a molecule or cell. For example, "modulate" may refer to increasing or decreasing the level and/or activity of all-trans-retinol:all-trans-13,14-dihydroretinol saturase.

Generally, other nomenclature used herein and many of the laboratory procedures used in cell culture, molecular genetics and nucleic acid chemistry and hybridization, which are described below, are those well known and commonly employed in the art. For example, standard techniques are used for recombinant nucleic acid methods, preparation of biological samples, isolation of polynucleotides, and the like.

The metabolism of vitamin A is a highly regulated process that generates essential mediators involved in the development and cellular differentiation of vertebrates. One particular enzyme involved in vitamin A metabolism, all-trans-retinol:all-trans-13,14-dihydroretinol saturase, is responsible for the oxidation of retinol to retinoic acid. More particularly, the enzyme all-trans-retinol:all-trans-13,14-dihydroretinol saturase is involved in the conversion of all-trans-retinol to all-trans-13,14-dihydroretinol, which may be further oxidized to form all-trans-13,14-dihydroretinoic acid. According to the present invention, it is believed that the level and/or activity of all-trans-retinol:all-trans-13,14-dihydroretinol saturase and enzymatic products thereof may play a role in the insulin secretory pathway and contribute to improved insulin production, insulin-responsive glucose uptake, and lipid metabolism.

Figure 6:
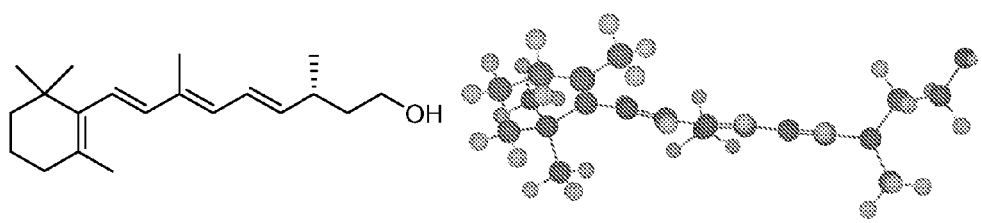
FIG. 6 shows the chemical structures of (13R)-all-trans-13,14-dihydroretinol and (13S)-all-trans-13,14-dihydroretinol in 2D projections (left) and 3D representation (right)
Figure 6:
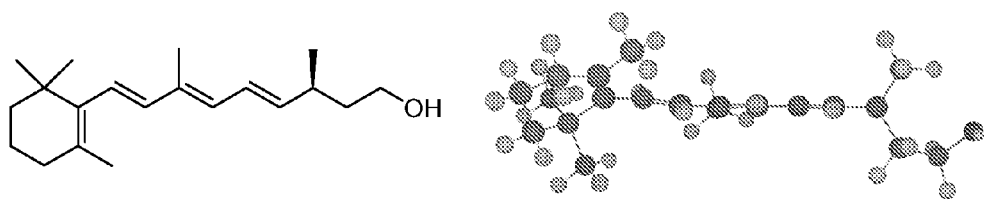
Figure 7:
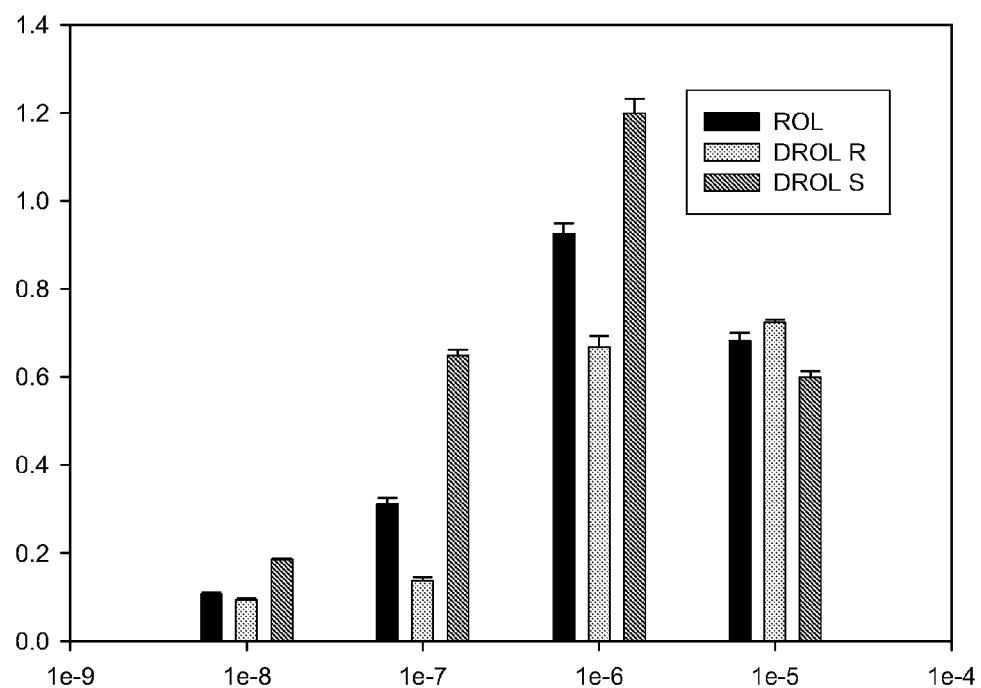
FIG. 7 is a histogram showing the activation of retinoic acid response element (RARE) by all-trans-retinol (ROL), (13R)-all-trans-13,14-dihydroretinol (DROL R) and (13S)-all-trans-13,14-dihydroretinol (DROL S)

In an aspect of the present invention, a pharmaceutical composition for treating a metabolic disease in a mammalian subject can comprise a therapeutically effective amount of at least one all-trans-13,14-dihydroretinoid or all-trans-13,14-dihydroretinoid derivative and a pharmaceutically acceptable carrier or diluent. As all-trans-13,14-dihydroretinol is a chiral compound it can exist in two different conformations, i.e., (13R)-all-trans-13,14-dihydroretinol also referred to as (R)-all-trans-13,14-dihydroretinol and (13S)-all-trans-13,14-dihydroretinol also referred to as (S)-all-trans-13,14-dihydroretinol (FIG. 6). Similarly, all-trans-13,14-dihydroretinoic acid can also exist in two different conformations, ie, (R)-all-trans-13,14-dihydroretinoic acid and (S)-all-trans-13,14-dihydroretinoic acid. In one aspect, the all-trans-13,14-dihydroretinoid or all-trans-13,14-dihydroretinoid derivative can comprise at least about 75%, 80%, 90%, 95%, or 99% (R)-all-trans-13,14-dihydroretinoid or (R)-all-trans-13,14-dihydroretinoid derivative so that the pharmaceutical composition is essentially free of (S)-all-trans-13,14-dihydroretinoid or (S)-all-trans-13,14-dihydroretinoid derivative and is not racemic. In one example, the (R)-all-trans-13,14-dihydroretinoid or (R)-all-trans-13,14-dihydroretinoid derivative can include at least about 75%, 80%, 90%, 95%, or 99% (R)-all-trans-13,14-dihydroretinol and/or (R)-all-trans-13,14-dihydroretinoic acid. In another aspect, the (R)-all-trans-13,14-dihydroretinoid or (R)-all-trans-13,14-dihydroretinoid derivative consists essentially of (R)-all-trans-13,14-dihydroretinol and/or (R)-all-trans-13,14-dihydroretinoic acid, or esters thereof.

In another aspect, the all-trans-13,14-dihydroretinoid or all-trans-13,14-dihydroretinoid derivative can comprise at least about 75%, 80%, 90%, 95%, or 99% (S)-all-trans-13,14-dihydroretinoid or (S)-all-trans-13,14-dihydroretinoid derivative so that the pharmaceutical composition is essentially free of (R)-all-trans-13,14-dihydroretinoid or (R)-alltrans-13,14-dihydroretinoid derivative and is not racemic. In one example, the (S)-all-trans-13,14-dihydroretinoid or (S)-all-trans-13,14-dihydroretinoid derivative can include at least about 75%, 80%, 90%, 95%, or 99% (S)-all-trans-13,14-dihydroretinol and/or (S)-all-trans-13,14-dihydroretinoic acid. In another aspect, the (S)-all-trans-13,14-dihydroretinoid or (S)-all-trans-13,14-dihydroretinoid derivative consists essentially of (S)-all-trans-13,14-dihydroretinol and/or (S)-all-trans-13,14-dihydroretinoic acid, or esters thereof.

As used herein, the term "pharmaceutically acceptable" means approved by a regulatory agent of the Federal or state government, or listed in the U.S. Pharmacopeia or other generally recognized pharmacopeia for use in animals, such as humans. The term "carrier" refers to a diluent, adjuvant, excipient, stabilizer, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can be employed as liquid carriers, particularly for injectable solutions. Suitable pharmaceutical excipients include starch, glucose, lactose, sucrose, gelatin, malt, rich, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Pharmaceutical compositions can take the form of solutions, suspensions, emulsions, tablets, pills, capsules, powders, sustained-release formulations, and the like. The composition can also be formulated as a suppository, with traditional binders and carriers such as triglycerides.

Oral formulations can include standard carriers such as pharmaceutical grades of mannitol, lactose, starch, magnesium stearate, sodium saccharine, cellulose, magnesium carbonate, and the like. Such compositions may contain a therapeutically effective amount of all-trans-13,14-dihydroretinoic acid, for example, typically in purified form, together with a suitable amount of carrier so as to provide a formulation proper for administration to a subject. Generally, the formulation should suit the mode of administration.

The pharmaceutical composition may also be formulated in accordance with routine procedures as a pharmaceutical composition adapted for intravenous administration to human beings. Typically, pharmaceutical compositions for intravenous administration are solutions in sterile isotonic aqueous buffer. Where necessary, the pharmaceutical composition can also include a solubilizing agent. Generally, the ingredients are supplied either separately or mixed together in unit dosage form as, for example, dry lyophilized powder or water-free concentrate in a hermetically sealed container (e.g., an ampoule or sachette) indicating the quantity of the active agent. Where the pharmaceutical composition is to be administered by infusion, the pharmaceutical composition can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

The pharmaceutical composition can also be formulated as neutral or salt forms. Pharmaceutically acceptable salts include those formed with free amino groups such as those derived from hydrochloric, phosphoric, acetic, oxalic, tartaric acids, and the like. Other pharmaceutically acceptable salts include those formed with free carboxyl groups, such as those derived from sodium, potassium, ammonium, calcium, ferric hydroxides, isopropylamine, triethylamine, 2-ethylamino ethanol, histidine, procaine, and the like.

In another aspect of the present invention, a method for treating a metabolic disease in a mammalian subject can comprise administering to the subject a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative in the subject. The pharmaceutical composition can be administered therapeutically (including prophylactically) in metabolic diseases involving a decreased (relative to normal or desired) level and/or activity of all-trans-retinol: all-trans-13,14-dihydroretinol saturase. For example, a pharmaceutical composition comprising at least one all-trans-13,14-dihydroretinoid, such as (R)-all-trans-13,14-dihydroretinol, can be administered to a subject having a metabolic disease where the all-trans-retinol:all-trans-13,14-dihydroretinol saturase polypeptide is under-expressed, genetically defective, or biologically hypoactive, as compared with a normal cell of that type.

In another aspect of the present invention, an (R)-all-trans-13,14-dihydroretinol or (S)-all-trans-13,14-dihydroretinol may be synthesized as described below and/or as described in Example 1.

By way of example, 13,14-dihydroretinoids can be synthesized as follows. B-Ionone can first be brominated with N-bromosuccinimide in $CCl_4$ followed by substitution of bromine with an acetoxyl group in hexamethylphosphoramide. The acetate ester of ionone can be hydrolyzed with $K_2CO_3$ in methanol:water, and then the hydroxyl group may be protected with tetra-butyldimethylsilyl group. The silylated 4-hydroxy-β-ionone (II) can then be condensed under Horner-Emmons conditions with triethylphosphonoacetate, and the ester of silyl-protected ethyl 4-hydroxy-β-ionylidene acetate reduced to alcohol with $LiAlH_4$. The alcohol can be acetylated with acetic anhydride in the presence of N,N-dimethylaminopyridine (DMAP). The silyl group can be removed by tetrabutylammonium fluoride, and the alcohol was oxidized to a ketone group with $MnO_2$ to give 15-acetoxy-4-oxo-β-ionylidene ethanol (III). Next, ester (III) can be hydrolyzed and the hydroxyl group brominated with $PBr_3$ in ether. The bromide may then be reacted with $PPh_3$ to give Wittig salt (IV), which may be further condensed with ethyl 4-oxo-3-methylbutyrate under conditions described previously (Moise, A. R. et al., 2004 J. Biol. Chem. 279, 10422-10432) to obtain a mixture of ethyl 13,14-dihyro-4-oxoretinoate isomers (V) with all-trans- as a major compound. The isomers may be separated by normal phase HPLC (HP1100, Beckman Ultrasphere Si 5μ, 10×250 mm, 5% ethyl acetate: hexane, and detection at 325 mm) and characterized by their UV, mass, and NMR spectra. NMR data can be recorded on a Bruker 500-MHz spectrometer using $CDCl_3$ as an internal standard. The order of elution may be as follows: 9,11-di-cis-, all-trans-, 9-cis, 11-cis-13,14-dihydro-4-oxoretinoate. To obtain free retinoic acid (VI), the ethyl ester can be hydrolyzed with NaOH in ethanol:$H_2O$. To obtain 13,14-dihydro-RAL (DRAL), previously prepared ethyl 13,14-dihydroretinoate can be reduced with diisobutyl aluminum hydride at −78° C. All-trans-4-oxo-DRA can have the following UV-visible absorbance spectrum in ethanol, $\lambda_{max}$=328 nm and shoulder at λ=256 nm, and in hexane, $\lambda_{max}$=314 nm and shoulder at λ=252 nm.

In another example, an all-trans-13,14-dihydroretinol can be synthesized as follows. All reagents can be purchased from Sigma or Fluka and used without additional purification.

Solvents can be dried under standard procedures prior to use. All operations with retinoids may be performed under dim red light unless otherwise specified. B-Ionone can be condensed with triethyl phosphonoacetate in anhydrous tetrahydrofuran in the presence of NaH to give ethyl trans-β-ionylideneacetate. This ester may then be reduced with LiAlH$_4$ to alcohol and reacted overnight with triphenylphosphine hydrobromide to give Wittig salt. Ethyl 4-oxo-3-methylcrotonate can be hydrogenated in methanol with H$_2$ using 10% palladium on carbon as a catalyst to yield ethyl 4-oxo-3-methylbutyrate, which may then be reacted with Wittig salt using t-BuOK as a base in anhydrous CH$_2$Cl$_2$ in the presence of 18-crown-6. The obtained mixture of ethyl 11-cis and all-trans-13,14-dihydroretinoates can be reduced with LiAlH$_4$ to 13,14-dihydroretinols, and all-trans-isomer separated from 11-cis-dihydroretinol by flash chromatography of silica gel using 5% ethyl acetate in hexane. NMR data can be recorded on a Bruker 500-MHz spectrometer using CDCl$_3$ as an internal standard. $^1$H NMR analysis of synthetic all-trans-13,14-dihydroretinol can yield: NMR (CDCl$_3$, δ, ppm) 6.41 (dd, 1H, H-12, J=11.3, 14.75 Hz), 6.10-6.12 (m, 3H, H-7, H-8, H-10, J=15.7 Hz), 5.6 (dd, 1H, H-11, J=8.34, 14.95 Hz), 3.67 (m, 2H, CH$_2$-15), 2.41 (m, 1H, H-13, J=6.7 Hz), 1.96 (m, 2H, CH$_2$-14), 1.90 (s, 3H, CH$_3$-9), 1.69 (s, 3H, CH$_3$-5), 1.46 (m, 2H, CH$_2$-2), 1.6 (m, 4H, CH$_2$-3, CH$_2$-4), 1.06 (d, 3H, CH$_3$-13 J=6.7 Hz), 1.00 (s, 6H, 2×CH$_3$-1).

In another aspect of the present invention, recombinant DNA techniques, such as those disclosed in PCT Pub. No. WO/06029398 A2, the entirety of which is herein incorporated by reference, may also be used to synthesize the at least one all-trans-13,14-dihydroretinoid and/or all-trans-13,14-dihydroretinoid derivative.

In another aspect of the present invention, a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative can be administered to a subject to promote lipolysis. "Lipolysis" refers to the breakdown (i.e., hydrolysis) of fats and oils, typically via adipocyte metabolism. The pharmaceutical composition may affect the activity and/or differentiation of at least one cell, such as a mature adipocyte, a pre-adipocyte, or an insulin-producing cell capable of promoting lipolysis.

As used herein, the term "adipocyte" refers to fat cells. Morphologically, adipocytes are round-shaped, triglyceride vesicle-containing cells. Biochemically, adipocytes express high levels of insulin receptor on their cell surface and exhibit a highly active insulin-mediated glucose transport signaling pathway involving GLUT4. In vivo, adipocytes are involved in the synthesis and storage of triglycerides and glucose metabolism. The term "pre-adipocyte" refers to adipocyte precursor cells that, under the action of hormones such as insulin and glucocorticoid, divide and differentiate into adipocytes. Morphologically, pre-adipocytes are fibroblast-looking (i.e., thin and spindle-shaped) and devoid of triglyceride vesicles in their cytoplasm. As compared to adipocytes, pre-adipocytes contain low levels of insulin receptor and relatively high levels of IGF-1 receptors for receiving mitogenic and differentiating signals. An "insulin-producing cell" refers to a cell that can synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. Examples of known insulin producing cells include β cells, which are located in the pancreatic islets in vivo.

In another aspect of the present invention, a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative may be administered to a cell having at least one receptor responsive to the level and/or activity of all-trans-retinol:all-trans-13,14-dihydroretinol saturase and enzymatic products thereof. The at least one receptor may include, for example, a G-protein-coupled receptor (GPCR or GPR). The GPCR may be characterized by a seven transmembrane domain containing seven transmembrane domains, three extracellular loops, and three intracellular loops, an N-terminal extracellular domain which may interact with a ligand, and a C-terminal intracellular domain which may interact with a G protein. More particularly, the GPCR can include GPR40, for example, which is expressed in pancreatic β cells and is known to be activated by medium and long-chain fatty acids, free fatty acids (e.g., linolenic and oleic acid), and thiazolidinedione drugs and in reference to this invention can be activated by all-trans-13,14-dihydroretinoic acid.

Figure 8:
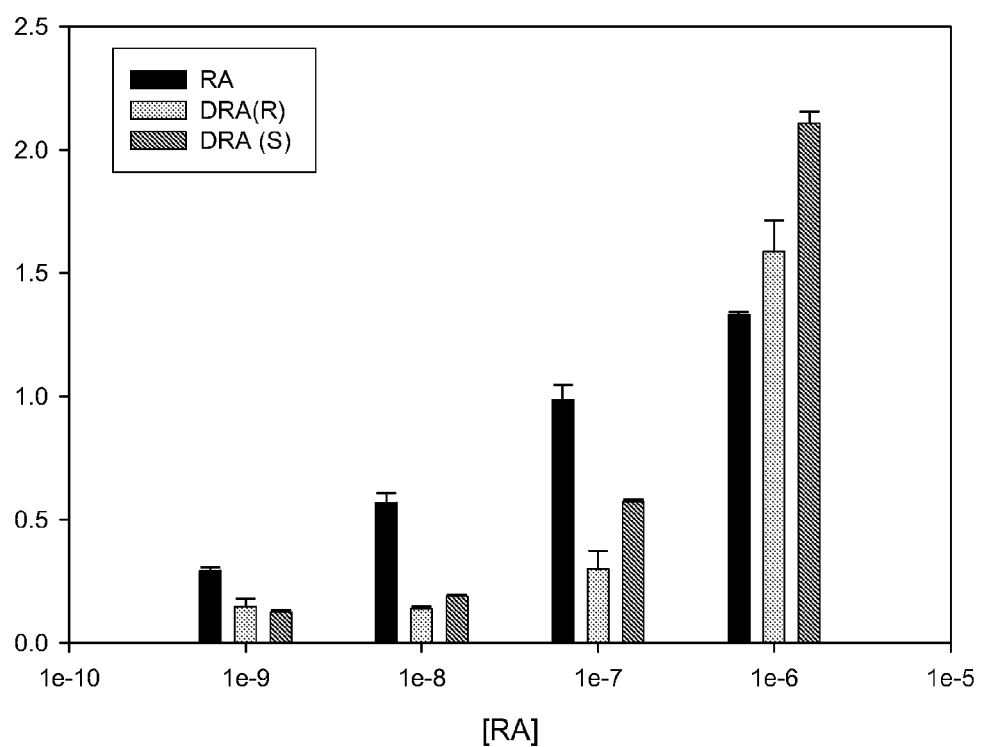
FIG. 8 is a histogram showing the activation of retinoic acid response element (RARE) by all-trans-retinoic acid (RA), (13R)-all-trans-13,14-dihydroretinoic acid (DRA R) and (13S)-all-trans-13,14-dihydroretinoic acid (DRA S)

The at least one receptor may also include a retinoic acid receptor (RAR), such as RAR-α, RAR-β and RAR-γ which, when activated, translocates to a cell nucleus, binds to hormone response element on DNA, and elicits expression or transexpresssion of gene products. Alternatively, at least one response element, such as the RAR response element (RARE), can be activated. As shown in FIG. 8, for example, both (R)-all-trans-13,14-dihydroretinoic acid and (S)-all-trans-13,14-dihydroretinoic acid can activate RAR. In another example (R)-all-trans-13,14-dihydroretinol and (S)-all-trans-13,14-dihydroretinol can also activate RAR. possibly by conversion to (R)-all-trans-13,14-dihydroretinoic acid and (S)-all-trans-13,14-dihydroretinoic acid, respectively.

In another aspect of the present invention, a method for increasing insulin production in a mammalian subject can comprise administering to the subject a pharmaceutical composition comprising at least one of all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative in the subject.

In an example of the method, a subject having a metabolic disease, such as type 1 diabetes, may be administered a therapeutically effective amount of a pharmaceutical composition comprising at least one all-trans-13,14-dihydroretinoid, all-trans-13,14-dihydroretinoid derivative, or agent capable of modulating the level of at least one all-trans-13,14-dihydroretinoid or all-trans-13,14-dihydroretinoid derivative. More particularly, the pharmaceutical composition may comprise (R)-all-trans-13,14-dihydroretinol, (S)-all-trans-13,14-dihydroretinol, (R)-all-trans-13,14-dihydroretinoic acid, (S)-all-trans-13,14-dihydroretinoic acid, or esters thereof, each individually in substantially non-racemic formulations or in combinations as substantially racemic formulations. The pharmaceutical composition may be administered to the subject intravenously, for example, whereafter a GPR40 receptor in at least one cell, such as pancreatic β cell, may be stimulated. Stimulation of the GPR40 receptor may increase the activity of the receptor and, in turn, increase insulin production and secretion in the pancreatic β cell. By improving insulin production in the subject, the symptoms associated with type 1 diabetes may be reduced and/or eliminated.

In another example of the method, a subject having a metabolic disease, such as obesity, may be administered a therapeutically effective amount of an agent capable of modulating the level of at least one all-trans-13,14-dihydroretinoid or all-trans-13,14-dihydroretinoid derivative. The agent can include, for example, an all-trans-retinol:all-trans-13,14-dihydroretinol saturase polypeptide, fragment, derivative or analog thereof. The polypeptides, fragments, derivatives, or analogs of all-trans-retinol:all-trans-13,14-dihydroretinol saturase may be derived from an animal (e.g., human, mouse, rat, pig, cow, dog, monkey, and the like), and can include naturally occurring amino acid sequence variants as well as those altered by substitution, addition or deletion of one or more amino acid residues that provide for functionally active molecules. For instance, an all-trans-retinol:all-trans-13,14-dihydroretinol saturase can include a human all-trans-retinol:all-trans-13,14-dihydroretinol saturase (GenBank Accession Number gi46329587), a mouse all-trans-retinol:all-trans-13,14-dihydroretinol saturase (GenBank Accession Number AY704159), or monkey (macaque) all-trans-retinol:all-trans-13,14-dihydroretinol saturase (GenBank Accession Number AY704159). Fragments, derivatives or analogs of all-trans-retinol:all-trans-13,14-dihydroretinol saturase polypeptides include, but are not limited to, those molecules comprising regions that are substantially similar to all-trans-retinol:all-trans-13,14-dihydroretinol saturase polypeptides or fragments thereof (e.g., at least 50% identity or similarity over an amino acid sequence of identical size), or when compared to an aligned sequence in which the alignment is done by a computer sequence comparison/alignment program known in the art.

The polypeptide(s) can be administered to the subject intravenously, for example, as a substantially pure composition of all-trans-retinol:all-trans-13,14-dihydroretinol saturase polypeptide or, alternatively, as a pharmaceutical composition. Administering the polypeptide(s) may increase the level of at least one all-trans-13,14-dihydroretinoid or all-trans-13,14-dihydroretinoid derivative in the subject. Consequently, the lipid metabolism of the subject may improve, for example, as evidenced by a decrease in visceral fat retention.

The present invention may also include other agents capable of modulating the level of at least one all-trans-13,14-dihydroretinoid or all-trans-13,14-dihydroretinoid derivative. Agents may additionally include, for example, at least one polynucleotide encoding all-trans-retinol:all-trans-13,14-dihydroretinol saturase. A nucleotide sequence coding for a all-trans-retinol:all-trans-13,14-dihydroretinol saturase polypeptide can be inserted into at least one cell of a subject using known recombinant DNA techniques, such as via an appropriate vector (i.e., a vector which contains the necessary elements for the transcription and translation of the inserted nucleotide sequence) harboring the nucleotide sequence. Other methods for delivering polynucleotides into a cell, such as direct DNA injection, may optionally be used and are known in the art.

Agents of the present invention also include compounds capable of modulating the level of at least one all-trans-13,14-dihydroretinoid or all-trans-13,14-dihydroretinoid derivative. Generally, suitable compounds can include any all-trans-retinol:all-trans-13,14-dihydroretinol saturase agonist or antagonist. For example, a suitable agonist can include a compound which binds to a polynucleotide encoding all-trans-retinol:all-trans-13,14-dihydroretinol saturase and increases the expression of an all-trans-retinol:all-trans-13,14-dihydroretinol saturase polypeptide. Alternatively, a suitable agonist can include a compound which binds to an all-trans-retinol:all-trans-13,14-dihydroretinol saturase polypeptide and increases the activity of the polypeptide. Suitable compounds may be identified using in vitro and/or in vivo assays. For example, in a typical in vivo assay, recombinant cells expressing polynucleotides encoding all-trans-retinol:all-trans-13,14-dihydroretinol saturase can be used to screen candidate compounds for those that affect all-trans-retinol:all-trans-13,14-dihydroretinol saturase expression. Effects on all-trans-retinol:all-trans-13,14-dihydroretinol saturase expression can include, for example, the synthesis of all-trans-13,14-dihydroretinoids.

Agents of the present invention can be administered to a human or other non-human vertebrate. Agent may be substantially pure, and a combination of agents may be used. Suitable routes for administering agents include, but are not limited to, intradermal, intramuscular, intraperitoneal, intravenous, subcutaneous, intranasal, intraocular, epidural and oral routes. The agents can be administered systemically or locally via a convenient route such as, for example, by infusion or bolus injection, by absorption through epithelial or mucocutaneous linings (e.g., oral mucosa, rectal and intestinal mucosa), and the like, and can be administered together with other functionally active agents.

Agents can be formulated as pharmaceutical compositions using techniques routinely used in the art. Such compositions can comprise, for example, a therapeutically effective amount of an agent and a pharmaceutically acceptable carrier.

The amount of the agent which will be effective in the treatment of a particular metabolic disease will depend on the route of administration and the seriousness of the disease, and should be decided according to the judgment of a qualified medical professional. In vitro assays can optionally be employed to help identify optimal dosage ranges. Effective doses may also be extrapolated from dose response curves derived from in vitro or animal model test systems.

In another aspect of the present invention, a method is provided for assessing whether a subject is afflicted with a metabolic disease. According to the method of the present invention, the level of a marker in a sample can be obtained from a subject. The marker can correspond to the level and/or activity of all-trans-retinol:all-trans-13,14-dihydroretinol saturase. After obtaining the marker, the level of the marker can be compared to a predetermined value to determine if the level and/or activity of all-trans-retinol:all-trans-13,14-dihydroretinol saturase in the subject is indicative of a metabolic disease. Individuals with decreased levels and/or activity of all-trans-retinol:all-trans-13,14-dihydroretinol saturase, for example, may be diagnosed with, or may be at an increased risk for having a metabolic disease. The ability to identify subjects having a metabolic disease, or being at risk for developing a metabolic disease, may permit appropriate and/or earlier targeting of such diseases with appropriate therapeutic modalities.

In another aspect of the present invention, the sample may be comprised of any biological tissue or fluid isolated from a subject, including, but not limited to, blood, plasma, serum, spinal fluid, lymph fluid, skin, respiratory, intestinal and genitourinary tracts, tears, saliva, milk, cells (including but not limited to blood cells), tumors, organs, and also samples of in vitro cell culture constituents.

In another aspect of the present invention, the marker corresponding to the level and/or activity of all-trans-retinol:all-trans-13,14-dihydroretinol saturase can be determined from the sample using any type of diagnostic technique(s) known in the art. For example, the level and/or activity of an all-trans-retinol:all-trans-13,14-dihydroretinol saturase polypeptide can be detected by first obtaining a sample (such as from a biopsy tissue) and then assaying the sample in vitro for RNA or polypeptide levels and/or the structure and/or activity of the expressed all-trans-retinol:all-trans-13,14-dihydroretinol saturase RNA or all-trans-retinol:all-trans-13,14-dihydroretinol saturase polypeptide. Many methods standard in the art can be employed including, but not limited to, immunoassays to detect and/or visualize all-trans-retinol:all-trans-13,14-dihydroretinol saturase polypeptides (e.g., Western blot, immunoprecipitation followed by SDS PAGE, immunocytochemistry, and the like) and/or hybridization assays to detect all-trans-retinol:all-trans-13,14-dihydroretinol saturase expression by detecting and/or visualizing all-trans-retinol:all-trans-13,14-dihydroretinol saturase mRNA (e.g., Northern blot assays, dot blots, in situ hybridization, quantitative reverse transcriptase-PCR, and the like).

In another aspect of the present invention, the marker can comprise the functional activity of all-trans-retinol:all-trans-13,14-dihydroretinol saturase polypeptides, fragments, derivatives, or analogs thereof, and may be determined using known techniques. For example, the ability of all-trans-retinol:all-trans-13,14-dihydroretinol saturase polypeptides to bind or compete with wild-type all-trans-retinol:all-trans-13,14-dihydroretinol saturase polypeptide for binding to anti-all-trans-retinol:all-trans-13,14-dihydroretinol saturase antibody may be assayed for using various immunoassays. Such assays include, but are not limited to, competitive and non-competitive assay systems using techniques such as radioimmunoassay, ELISA "sandwich" immunoassays, immunoradiometric assays, gel diffusion precipitin reactions, immunodiffusion assays, in situ immunoassays (using colloidal gold, enzyme or radioisotope labels, and the like), Western blots, precipitation reactions, agglutination assays (e.g., gel agglutination assays, hemagglutination assays), complement fixation assays, immunofluorescence assays, protein A assays, immunoelectrophoresis assays, and the like.

In another aspect of the present invention, the marker corresponding to the level and/or activity of all-trans-retinol:all-trans-13,14-dihydroretinol saturase can comprise a polynucleotide encoding a mutant all-trans-retinol:all-trans-13,14-dihydroretinol saturase polypeptide. The polynucleotide encoding the mutant all-trans-retinol:all-trans-13,14-dihydroretinol saturase polypeptide may include a "genetic polymorphism" which, as used herein, refers to a difference in a nucleotide sequence of a gene among individuals in a population of the same species of an organism. The difference in a nucleotide sequence that constitutes a genetic polymorphism is not limited to a specific form. For example, various types of genetic polymorphisms, such as base substitutions, deletion mutations, and/or insertion mutations may comprise the genetic polymorphism.

Determining whether a subject has a metabolic disease, or is at risk of developing a metabolic disease, may be generally performed by determining whether there is a mutation in the polypeptide encoding an all-trans-retinol:all-trans-13,14-dihydroretinol saturase polypeptide. Various methods are known in the art for detecting a mutation in a polynucleotide. Typically, nucleic acid amplification methods in which a primer having a sequence complementary to a nucleic acid template can be employed. Known amplification methods include, for example, PCR, strand displacement amplification, self-sustained sequence replication, nucleic acid sequence based amplification, transcription-mediated amplification, and isothermal and chimeric primer-initiated amplification. Other nucleic acid-based diagnostic techniques, such as DNA microarray technology and/or Southern blotting, may be used to detect a mutant polynucleotide.

Figure 9:
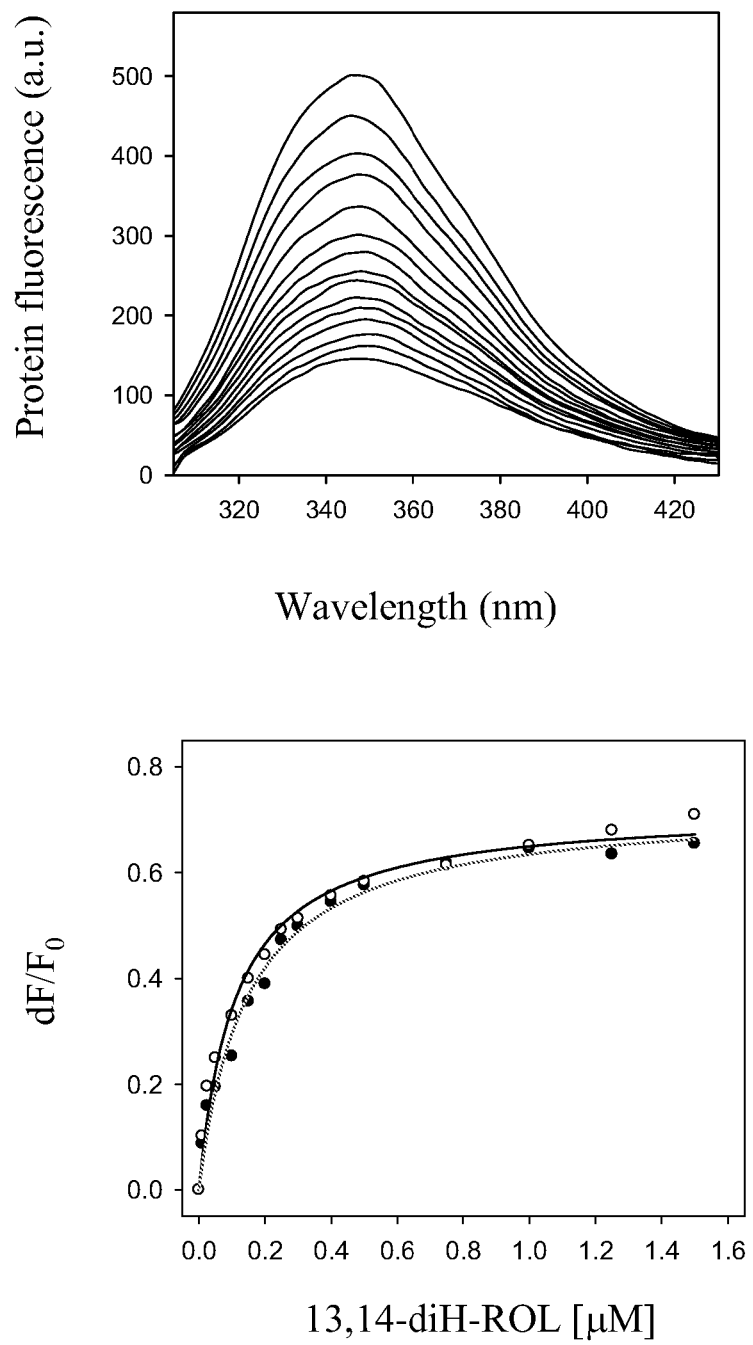
FIG. 9 is a series of graphs showing the binding of (R)-all-trans-13,14-dihydroretinol and (S)-all-trans-13,14-dihydroretinol to RBP4, as determined by fluorescence quenching.

In another aspect of the present invention, the marker corresponding to the level and/or activity of an all-trans-retinol:all-trans-13,14-dihydroretinol saturase polypeptide may comprise a metabolite, such as a retinoid, associated with all-trans-retinol:all-trans-13,14-dihydroretinol saturase activity. The marker can include, for example, a retinoid having a saturated $C_{13-14}$ double bond. More particularly, the retinoid having a saturated $C_{13-14}$ double bond can include all-trans-13,14-dihydroretinol and/or all-trans-13,14-dihydroretinoic acid. As shown in FIG. 9, (R)-all-trans-13,14-dihydroretinol, and (S)-all-trans-13,14-dihydroretinol are associated with the carrier protein retinol binding protein 4 (RBP4). Increased levels of RBP4 are associated with the metabolic syndrome, diabetic disease and correlate with increased insulin resistance, obesity and visceral adiposity. Various techniques known in the art may be used to detect dihydroretinoid metabolite levels in a tissue sample, including, but not limited to, chromatography-based methods, electrophoresis and sedimentation, mass spectroscopy, and/or antibody-based methods. Chromatography-based method include, but are not limited to, partition chromatography, adsorption chromatography, paper chromatography, thin-layer chromatography, gas-liquid chromatography, gel chromatography, ion-exchange chromatography, affinity chromatography, and hydrophobic interaction chromatography. Mass spectroscopy (MS)-based methods can include, for example, atmospheric pressure chemical ionisation MS, chemical ionisation MS, electron impact MS, electrospray ionisation MS, fast atom bombardment MS, field desorption/field ionisation MS, matrix assisted laser desorption ionisation MS, and thermospray ionisation MS. Antibody-based methods can include any one or combination of the assays, such as an ELISA, discussed above.

In another aspect of the present invention, the level of the marker can be compared to a predetermined value to determine whether a subject has a metabolic disease or is at risk of developing a metabolic disease. The predetermined value can be based upon the marker levels in comparable samples obtained from the general population or from a select population of humans. For example, the select population may be comprised of apparently healthy individuals. "Apparently healthy," as used herein, means individuals who have not previously had any signs or symptoms indicating the presence of a metabolic disease.

The predetermined value can be related to the value used to characterize the level of the marker in a sample obtained from a subject with a metabolic disease. Thus, if the level of the marker is a representative value, such as an arbitrary unit obtained from a cytogram, the predetermined value may also be based on the representative value.

The predetermined value can take a variety of forms. The predetermined value can be a single cut-off value, such a as a median or mean. The predetermined value can be established based upon comparative groups such as where the level of the marker (e.g., the level of all-trans-retinol:all-trans-13,14-dihydroretinol saturase) in one defined group is half the level of the corresponding marker in another defined group. The predetermined value can be a range, for example, where the general population is divided equally (or unequally) into groups, or into quadrants, the lowest quadrant being individuals with the lowest levels of the marker, the highest quadrant being subjects with the highest levels of the marker.

The predetermined value can be derived by determining the respective marker level in the general population. Alternatively, the predetermined value can be derived by determining the respective marker level in a select population. Accordingly, the predetermined values selected may take into account the category in which a subject falls. Appropriate ranges and categories can be selected with no more than routine experimentation by those of ordinary skill in the art.

Predetermined values, such as mean levels, median levels, or "cut-off" levels, are established by assaying a large sample of subjects in the general population, or the select population, using a statistical model such as the predicative value method for selecting a positivity criterion or receiver operator characteristic curve that defines optimum specificity (highest true negative rate) and sensitivity (highest true positive rate). The levels of each marker in a sample may be compared to a single predetermined value or to a range of predetermined values. If the level of the marker in the sample is lower than a predetermined value or range of predetermined values, then a subject may be diagnosed with a particular metabolic disease or, alternatively, diagnosed as being at risk for developing a metabolic disease.

The extent of the difference between the marker level and the predetermined value may also be useful for characterizing the extent of a metabolic disease. For example, a marker level may be below a certain cut-off value or in the higher tertile or quartile of a "normal range." In this instance, such a marker level may indicate an elevated risk for developing a metabolic disease.

The following examples are for the purpose of illustration only and are not intended to limit the scope of the claims, which are appended hereto.

Example 1

Diastereoselective synthesis of the (R)- and (S)-13,14-dihydroretinol enantiomers Synthesis of (R)-all-trans-13,14-dihydroretinol follows Suzuki coupling as the connective method to construct the polyene skeleton of the target 13,14-dihydroretinol enantiomers due to its proven performance in the synthesis of sensitive conjugated polyenes (Torrado, A. et al. *Tetrahedron* 51:2435-2454 (1995)). The chirality was transferred from that of the γ-alkoxy group in (4R)- and (4S)-4,5-(O-isopropylidene)pent-2-enoate enantiomers 1 using as asymmetric induction step the addition of organolithium reagents (Leonard, J. et al. *Tetrahedron* 51:12843-12858 (1995)). Only the sequence based on the latter, depicted in Scheme 1, and leading to the biological material will be discussed.

Scheme 1.

Scheme 1[a]. Preparation of (R)-13,14-dihydroretinol.

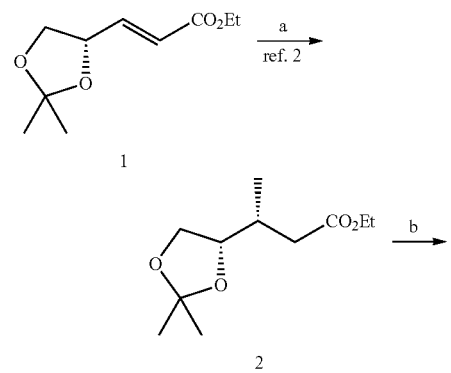

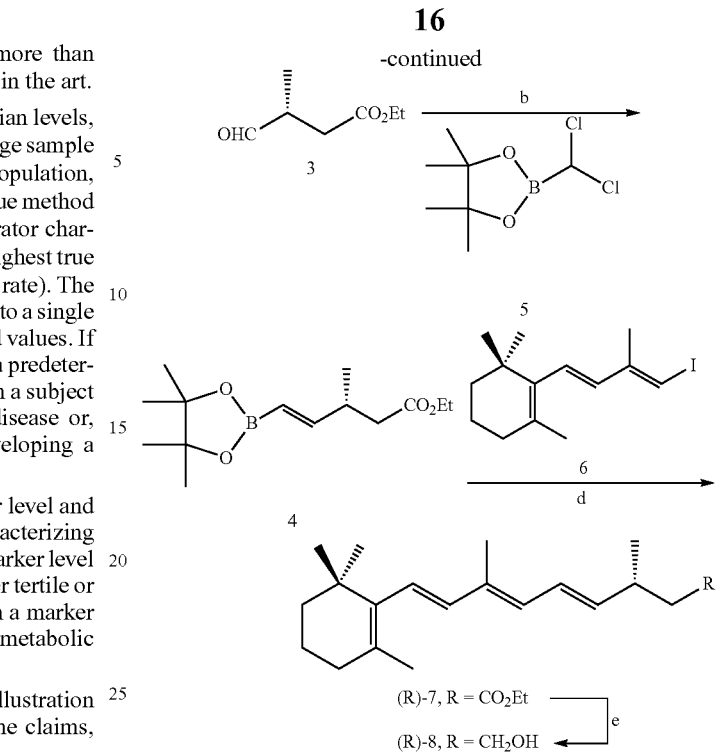

Reagents and conditions:
(a) MeLi, THF, -78° C.
(b) H$_5$IO$_6$, 1:1 THF/Et$_2$O, 25° C., 14 h, 68%.
(c) CrCl$_2$, THF, 2-(dichloromethyl)-4,4,5,5-tetramethyl-1,3,2-dioxaborolane 5, LiI, 25° C., 14 h, 68%.
(d) iodide 6, Pd(PPh$_3$)$_4$, THF, 10% aq. TlOH, 25° C., 2 h, 55%.
(e) DIBAL-H, THF, -78° C., 2 h, 73%.

The addition of organolithium reagents to ethyl (4R)- and (4S)-4,5-(O-isopropylidene)pent-2-enoate enantiomers 1 and other γ-alkoxy-α,β-unsaturated esters has been demonstrated to afford a mixture of the 1,4- and 1,2/1,4-addition products in 70% yield, where the relative configuration of the alkoxy and methyl groups in the 1,4 product 2 is syn. Ester 2, from the reaction of (S)-1, was treated with peryodic acid (Wu, W-L. et al. *J. Org. Chem.* 58:3586-3588 (1993); Xie, M. et al. *J. Org. Chem.* 61:5178-5179 (1996)) to effect deprotection of the isopropylidene acetal and concomitantly induce the oxidative cleavage of the glycol to afford aldehyde (R)-3.

The preparation of the alkenylpinacolatoboronate (R)-4 involved the treatment of (R)-3 with the organochromium intermediate generated by treatment of dichloromethylboron (pinacolate) 5 (Takai, K. et al. *Synlett* 963-964 (1995)) with CrCl$_2$ in the presence of LiI, according to the modified Takai procedure reported by Jacobsen (Harem, I. T. et al. *J. Am. Chem. Soc.* 126:706-707 (2004)). The Suzuki coupling with known trienyliodide 6 (Negishi, E. et al. *J. Am. Chem. Soc.* 102:3298-3299 (1980); Negishi, E. et al. *Org. Synth.* 64:44-47 (1985)) proceeded with catalysis of Pd(PPh$_3$)$_4$ under the mediation of TlOH (Uenishi, J. et al. *J. Am. Chem. Soc.* 109:4756-4768 (1987)) to provide tetraene ester (R)-7. Lastly, reduction of ester 7 with DIBAL-H afforded (R)-13,14-dihydroretinol (R)-8. Analogous sequence furnished (S)-13,14-dihydroretinol (S)-8 from (4R)-4,5-(O-isopropylidene)pent-2-enoate 1.

Determination of the enantiomeric excess of the target compounds was based on HPLC separation using a Chiralcel OD-H 0.46×15 cm column, which afforded an ee value of >96% for each enantiomer of 8.

Reagents and solvents were purchased as reagent-grade and used without further purification unless otherwise stated. Solvents were dried according to standard methods and distilled before use. All reactions were performed in oven-dried or flame-dried glassware under an inert atmosphere of Ar unless otherwise stated. Chromatography refers to flash chromatography (FC) on $SiO_2$ 60 (230-400 mesh) from Merck, head pressure of ca. 0.2 bar. TLC: $UV_{254}$ $SiO_2$-coated plates from Merck, visualization by UV light (254 nm) or by coloring with 15% ethanolic phosphomolybdic acid solution. NMR spectra were recorded in a Bruker AMX400 (400.13 MHz and 100.61 MHz for proton and carbon, respectively) spectrometer at 298 K with residual solvent peaks as internal reference and the chemical shifts are reported in δ [ppm], coupling constants J are given in [Hz] and the multiplicities assigned with DEPT experiments and expressed as follows: s=singlet, d=doublet, t=triplet, q=quartet, m=multiplet. Electronic Impact ionization (EI) mass spectra were recorded on a VG-Autospec M instrument. HPLC purification and ee determination was carried out on a Waters 515 HPLC system with 717plus autosampler, PDA Waters 996 detector set to 288 nm, using a Chiralcel OD-H 0.46×15 cm column, 2.5% hexane/EtOH with a flow rate of 0.5 mL/min. Specific rotations were determined in a JASCO P-1020 polarimeter.

Ethyl (3R)-3-Methyl-4-oxobutanoate (R)-3

To a solution of (R)-ethyl 3-[(S)-2,2-dimethyl-1,3-dioxolan-4-yl]butanoate (3R,4S)-2 (0.065 g, 0.30 mmol) in a 1:1 THF/$Et_2O$ mixture (10.7 mL), was added $H_5IO_6$ (0.137 g, 0.60 mmol). After stirring for 14 h, the solids were filtered and the solvent was evaporated. The residue was diluted in $CH_2Cl_2$ (6.5 mL) and washed with $H_2O$ (3×) and brine (3×). The organic layer was dried ($Na_2SO_4$) and the solvent was evaporated. The residue was purified by column chromatography (silica gel, 95:5 hexane/ethyl acetate) to afford 29 mg (68%) of colourless oil identified as ethyl (3R)-3-methyl-4-oxobutanoate (R)-3. $[\alpha]_D^{20}$+6.71 (c 0.034, MeOH). $^1$H-NMR (400.16 MHz, $CDCl_3$): δ 9.70 (s, 1H, $H_4$), 4.15 (q, J=7.0 Hz, 1H, $OCH_2CH_3$), 2.9-2.8 (m, 1H, $H_3$), 2.73 (dd, J=16.4, 7.0 Hz, 1H, $H_2$), 2.37 (dd, J=16.4, 6.4 Hz, 1H, $H_2$), 1.26 (t, J=7.2 Hz, 3H, $OCH_2CH_3$), 1.19 (d, J=7.3 Hz, 3H, $C_3$—$CH_3$) ppm. $^{13}$C-NMR (100.61 MHz, $CDCl_3$): δ 202.7 (d), 171.7 (s), 60.7 (t), 42.5 (d), 34.9 (t), 14.1 (q), 13.3 (q) ppm. MS (Er): m/z (%) 145 ($M^+$+1, 26), 143 (11), 116 (29), 101 (17), 99 (100), 97 (11), 88 (27), 73 (49), 71 (52). HRMS ($EI^+$): Calcd. for $C_{17}H_{13}O_3$ ($M^+$+1), 145.0865. found, 145.0869.

Ethyl (3S)-3-Methyl-4-oxobutanoate (S)-3

Following the same procedure for the oxidative cleavage with $H_5IO_6$, the reaction of (S)-ethyl 3-[(R)-2,2-dimethyl-1,3-dioxolan-4-yl]butanoate (3S,4R)-2 (0.1 g, 0.46 mmol) with $H_5IO_6$ (0.211 g, 0.92 mmol) in 1:1 THF/$Et_2O$ (16.5 mL) afforded, after purification by column chromatography (silica gel, 95:5 hexane/ethyl acetate), 47 mg (70%) of a colourless oil identified as ethyl (3S)-3-methyl-4-oxobutanoate (S)-3. $[\alpha]_D^{20}$–5.47 (c 0.03, MeOH).

Ethyl (3R,4E)-3-Methyl-5-(4,4,5,5-tetramethyl-1,3,2-dioxaborolan-2-yl)pent-4-enoate (R)-4

To a solution of anhydrous $CrCl_2$ (0.59 g, 4.8 mmol) in THF (6 mL), were added a solution of (R)-ethyl 3-methyl-4-oxobutanoate (R)-3 (84.3 mg, 0.6 mmol) and immediately 2-(dichloromethyl)-4,4,5,5-tetramethyl-1,3,2-dioxaborolane 5 (0.253 g, 1.2 mmol) in THF (0.8 mL), followed by dropwise addition of a solution of LiI (0.32 g, 2.4 mmol) in THF (0.5 mL). After stirring for 14 h, the reaction was poured onto ice/water and extracted with $Et_2O$ (2×) and $CH_2Cl_2$ (2×). The combined organic layers were dried ($Na_2SO_4$) and the solvent was evaporated. The residue was purified by column chromatography (silica gel, 97:3 hexane/ethyl acetate) to afford 107 mg (68%) of a colourless oil identified as ethyl (3R,4E)-3-methyl-5-(4,4,5,5-tetramethyl-1,3,2-dioxaborolan-2-yl)pent-4-enoate (R)-4. $^1$H-NMR (400.16 MHz, $CDCl_3$): δ 6.56 (dd, J=18.0, 6.5 Hz, 1H, $H_4$), 5.43 (dd, J=18.0, 1.3 Hz, 1H, $H_5$), 4.13 (q, J=7.1 Hz, 1H, $OCH_2CH_3$), 2.76 (m, 1H, $H_3$), 2.41 (dd, J=15.0, 6.5 Hz, 1H, $H_2$), 2.26 (dd, J=15.0, 8.1 Hz, 1H, $H_2$), 1.26 (s, 15H, —$OC(CH_3)_2C(CH_3)_2O$—)+$OCH_2CH_3$), 1.06 (d, J=6.7 Hz, 3H, $C_3$—$CH_3$) ppm. $^{13}$C-NMR (100.61 MHz, $CDCl_3$): δ 172.4 (s), 157.1 (d, 2×), 83.1 (s, 2×), 60.2 (t), 40.6 (t), 35.8 (d), 24.7 (4×, q), 19.1 (q), 14.2 (q) ppm. MS ($EI^+$): m/z (%) 268 ($M^+$, 3), 253 (32), 222 (11), 207 (12), 181 (11), 180 (11), 179 (21), 168 (52), 167 (23), 165 (13), 153 (18), 145 (11), 141 (24), 140 (35), 39 (20), 138 (11), 137 (13), 125 (23), 124 (100), 123 (25), 111 (10) 101 (16), 97 (38), 96 (78) 95 (30), 88 (12), 86 (63), 85 (24), 84 (97), 81 (25), 78 (11). HMRS ($EI^+$): Calcd for $C_{14}H_{25}BO_4$, 268.1846. found, 268.1844.

Ethyl (3S,4E)-3-Methyl-5-(4,4,5,5-tetramethyl-1,3,2-dioxaborolan-2-yl)pent-4-enoate (S)-4

Following the same procedure for the preparation of pinacol boronates, the reaction of ethyl (S)-3-methyl-4-oxobutanoate (S)-3 (0.057 g, 0.40 mmol) with $CrCl_2$ (0.39 g, 3.18 mmol), 2-(dichloromethyl)-4,4,5,5-tetramethyl-1,3,2-dioxaborolane 5 (0.168 g, 0.80 mmol) and LiI (0.21 g, 1.59 mmol) in THF (6 mL) afforded, after purification by column chromatography (silica gel, 97:3 hexane/ethyl acetate), 69 mg (65%) of a colourless oil identified as ethyl (3S,4E)-3-methyl-5-(4,4,5,5-tetramethyl-1,3,2-dioxaborolan-2-yl)pent-4-enoate (S)-4.

Ethyl (13R)-13,14-Dihydroretinoate (R)-7

To a solution of 2-[(1E,3E)-4-iodo-3-methylbuta-1,3-dienyl]-1,3,3-trimethylcyclohex-1-ene 6 (0.091 g, 0.29 mmol) in THF (1.7 mL) was added $Pd(PPh_3)_4$ (0.026 g, 0.022 mmol). After stirring for 5 min, a solution of ethyl (3R,4E)-3-methyl-5-(4,4,5,5-tetramethyl-1,3,2-dioxaborolan-2-yl)pent-4-enoate (R)-4 (0.06 g, 0.22 mmol) in THF (0.6 mL) and 10% aqueous T10H (2.37 mL, 1.07 mmol) were sequentially added. After stirring the resulting mixture for 2 h at 25° C., it was diluted with $Et_2O$ (2 mL) and extracted with $Et_2O$ (3×). The combined organic layers were washed with brine (3×), dried ($Na_2SO_4$) and the solvent was evaporated. The residue was purified by column chromatography (silica gel, 98:2 hexane/ethyl acetate) to afford 40.4 mg (55%) of a yellow oil identified as ethyl (13R)-13,14-dihydroretinoate (R)-7. $[\alpha]_D^{20}$–27.57 (c 0.02, MeOH). $^1$H-NMR (400.16 MHz, $(CD_3)_2CO$): δ 6.48 (ddd, J=15.1, 11.1, 1.1 Hz, 1H), 6.13 (d, J=16.3 Hz, 1H), 6.09 (d, J=16.3 Hz, 1H), 6.02 (d, J=11.1 Hz, 1H), 5.69 (dd, J=15.0, 7.6 Hz, 1H), 4.07 (q, J=7.1 Hz, 2H), 2.74 (sep, J=7.0 Hz, 1H), 2.4-2.3 (m, 1H), 2.1-2.0 (m, 2H), 2.02 (t, J=6.0 Hz, 1H), 1.7-1.6 (m, 2H), 1.6-1.5 (m, 2H), 1.21 (t, J=7.1 Hz, 3H), 1.08 (d, 3H, J=6.8 Hz), 1.01 (s, 6H) ppm. $^{13}$C-NMR (100.61 MHz, $(CD_3)_2CO$): δ 171.3 (s), 138.3 (d), 137.8 (d), 137.6 (s), 133.8 (s), 129.9 (d), 128.3 (s), 125.7 (d), 125.5 (d), 59.5 (t), 41.1 (t), 39.3 (t), 33.8 (2×, d, s), 32.5 (t), 28.2 (2×, q), 20.9 (q), 19.5 (q), 18.9 (t), 13.6 (q), 11.6 (q) ppm. MS ($EI^+$): m/z (%). 330 ($M^+$, 15), 213 (24), 199 (27), 185 (62), 171 (36), 157 (36), 143 (30), 129 (79), 121 (21), 119

(23), 115 (31), 111 (33), 110 (21), 98 (29), 97 (68), 96 (32), 73 (100). HRMS (EI+): Calcd. for $C_7H_{12}O_3$, 330.2559. found, 330.2552.

Ethyl (13S)-13,14-Dihydroretinoate (S)-7

Following the same procedure for the Suzuki cross coupling, the reaction of (3S,4E)-3-methyl-5-(4,4,5,5-tetramethyl-1,3,2-dioxaborolan-2-yl)pent-4-enoate (S)-4 (0.03 g, 0.112 mmol) with 2-[(1E,3E)-4-iodo-3-methylbuta-1,3-dienyl]-1,3,3-trimethylcyclohex-1-ene 6 (0.045 g, 0.145 mmol), $Pd(PPh_3)_4$ (0.013 g, 0.011 mmol) and 10% aqueous T10H (1.19 mL, 0.54 mmol) in THF (1.15 mL) afforded, after purification by column chromatography (silica gel, 98:2 hexane/ethyl acetate), 20 mg (54%) of a yellow oil identified as ethyl (13S)-13,14-dihydroretinoate (S)-7. $[\alpha]_D^{20}$+25.78 (c 0.4, MeOH).

(13R)-13,14-Dihydroretinol (R)-8

Dibal-H (0.13 mL, 1M in hexane, 0.13 mmol) was added to a cooled (−78° C.) solution of (13R)-13,14-dihydroretinoate (R)-7 (20.1 mg, 0.061 mmol) in THF (6 mL), and the resulting suspension was stirred for 2 h. After careful addition of $H_2O$, the mixture was extracted with $Et_2O$ (3×) and the organic layers were dried ($Na_2SO_4$) and concentrated. The residue was purified by column chromatography (silica gel, 90:10 hexane/ethyl acetate) to afford 12.7 mg (73%) of a colorless oil identified as (13R)-13,14-dihydroretinol (R)-8. $[\alpha]_D^{20}$−12.23 (c 0.09, MeOH). $^1$H-NMR (400.16 MHz, $CDCl_3$): δ 6.41 (dd, J=14.9, 11.2 Hz, 1H), 6.11 (d, J=16.1 Hz, 1H), 6.04 (d, J=16.1 Hz, 1H), 5.99 (d, J=11.1 Hz, 1H), 5.60 (dd, J=14.9, 8.3 Hz, 1H), 3.66 (t, J=6.2 Hz, 2H), 2.5-2.4 (m, 1H), 2.1-2.0 (m, 2H), 1.90 (s, 3H), 1.69 (s, 3H), 1.7-1.6 (m, 4H), 1.6-1.5 (m, 2H), 1.05 (d, J=6.8 Hz, 3H), 1.00 (s, 6H) ppm. $^{13}$C-NMR (100.61 MHz, $(CD_3)_2CO$): 140.6 (d), 137.9 (d), 137.7 (s), 133.1 (s), 130.3 (d), 128.1 (s), 125.2 (d), 125.1 (d), 59.4 (t), 39.9 (t), 39.3 (t), 33.8 (s), 33.6 (d), 32.5 (t), 28.2 (q, 2×), 20.9 (t), 20.1 (q), 18.9 (q), 11.6 (q) ppm. MS (Er): m/z (%) 288 (M+, 82), 273 (24), 215 (34), 187 (52), 185 (35), 175 (32), 173 (50), 171 (45), 159 (91), 145 (77), 133 (64), 131 (58), 121 (53), 119 (100), 107 (50), 105 (96), 95 (65). HRMS (Er): Calcd. for $C_7H_{12}O_3$, 288.2453. found, 288.2463.

(13S)-13,14-Dihydroretinol (S)-8

Following the same procedure, the reaction of (13S)-13,14-dihydroretinoate (13S)-7 (9.3 mg, 0.028 mmol) with Dibal-H (0.084 mL, 1M in hexane, 0.084 mmol) in THF (3 mL) afforded, after purification by column chromatography (silica gel, 90:10 hexane/ethyl acetate), 8.0 mg (99%) of a colorless oil identified as (13S)-13,14-dihydroretinol (S)-8. $[\alpha]_D^{20}$+10.76 (c 0.13, MeOH).

Example 2

Dose Response and Activation of GPR40 by all-trans-13,14-dihydroretinoic acid

The activation of GPR40 by all-trans-13,14-dihydroretinoic acid is studied in vitro by measuring the calcium flux and internalization of GPR40 in response to all-trans-13,14-dihydroretinoic in GPR40-expressing recombinant cells. In collaboration with Dr. de Lera University of Vigo, Spain, we have produced synthetic enantiomerically pure (R) or (S) all-trans-13,14-dihydroretinol and all-trans-13,14-dihydroretinoic acid and we have determined the stereospecificity of the RetSat catalyzed reaction. Activation of GPR40 by all-trans-13,14-dihydroretinoic acid leading to secretion of insulin is studied by measuring the level of secreted insulin from INS-1 insulinoma cells or from primary pancreatic β-cells primed with all-trans-13,14-dihydroretinoic acid. Our results demonstrate that injection of all-trans-13,14-dihydroretinol in wild type mice results in prolonged hypoglycemia. These results suggest that a dihydroretinoid metabolite may play a direct role in secretion of insulin.

The effects of dihydroretinoids on glucose sensitivity and insulin secretion from pancreatic-β cell is also studied. Such studies should contribute to our molecular understanding of the physiological role of dihydroretinoids. Plasma insulin levels of mice gavaged with all-trans-13,14-dihydroretinoic acid are used to establish the in vivo dose response curve. The specificity of the interaction and receptor-dependence of the observed effects of all-trans-13,14-dihydroretinoic acid are examined by treating mice and tissues derived from GPR40$^{−/−}$ mice (Deltagen) with all-trans-13,14-dihydroretinoic acid. These experiments should provide proof that the in vivo effects of all-trans-13,14-dihydroretinoic acid are mediated by GPR40.

We also propose to examine the in vivo role of dihydroretinoids in insulin secretion or in determining insulin tissue sensitivity. To do so, acute insulin release in overnight fasted animals loaded with glucose is examined. Tail vein plasma glucose levels are measured and intraorbital bleeds of anesthetized mice are used to determine plasma insulin levels by ELISA. Insulin sensitivity is assessed using the euglycemic hyperinsulinemic clamp technique and glucose output is measured using the pancreatic glucose clamp technique. We have established the absolute configuration of the naturally occurring dihydroretinoids of the R (endogenous) and S (non-endogenous) enantiomers of all-trans-13,14-dihydroretinoic acid are employed to establish the stereospecificity of the interaction with GPR40. By using (R) or (S) all-trans-13,14-dihydroretinol or all-trans-13,14-dihydroretinoic acid as well as various downstream metabolites of all-trans-13,14-dihydroretinol, metabolic changes affecting insulin secretion and/or response may be induced. Mice are treated daily for two weeks by gavage or injection with compound dissolved in vegetable oil for gavage or dimethyl-sulfoxide for i.p. Their glucose tolerance response is examined following an overnight fast. Metabolic parameters is monitored to assess effectiveness and to look for any signs of toxicity. These assays are offered as a phenotyping service by the MMPC at Case Western Reserve University.

Example 3

Various animal models of metabolic disease are employed to study the feasibility of using dihydroretinoid metabolites in the treatment of diabetic disease. Mice are maintained on normal chow with the exception of the diet-induced obesity model (DIO), which are fed a high-fat diet. Mice are gavaged daily for a week using an oil emulsion of (13R) all-trans-13,14-dihydroretinol, all-trans-13,14-dihydroretinyl acetate, all-trans-13,14-dihydroretinoic acid or all-trans-13,14-dihydroretinoate ethyl ester. Fasting glucose and insulin levels are monitored before and after treatment. Glucose tolerance tests and Insulin tolerance tests are then be performed to determine if any positive changes have occurred as a result of treatment. These studies are complemented by using controls based on vehicle control, comparison with gavage with retinol or retinoic acid as well as by comparing the effects of biologically active, endogenous (R) enantiomers to the non-endogenous (S) enantiomers of the particular dihydroretinoid used in treatment.

Example 4

RetSat−/− mice have an impaired glucose tolerance response consistent with a reduced first-phase insulin secretion. It is important to determine if the metabolic defects observed in RetSat−/− mice can be attributed to the absence of dihydroretinoid metabolites. The metabolic defects observed in RetSat−/− mice by administration of all-trans-13,14-dihydroretinol which they lack are corrected. By using various downstream metabolites of all-trans-13,14-dihydroretinol to rescue the phenotype of RetSat−/− mice we can determine which of the dihydroretinoid metabolite is responsible for the observed effect, hence the nature of the true bioactive dihydroretinoid metabolite. This identification should greatly advance the knowledge of the relationship between vitamin A and metabolism. We hypothesize that it is the absence of dihydroretnoids which leads to a reduced insulin secretion response in RetSat−/− mice. We propose to examine the rate of insulin secretion in RetSat−/− mice using hyperglycemic clamp and arginine-stimulated insulin secretion assays. The secretion of insulin in vitro in pancreatic islet cells isolated from RetSat−/− mice are also examined. The metabolic defects observed in RetSat−/− mice by administration of all-trans-13,14-dihydroretinol which they lack are corrected by using various downstream metabolites of all-trans-13,14-dihydroretinol. The administration of all-trans-13,14-dihydroretinol should result in recovery and activation of insulin secretion in RetSat−/− mice.

Example 5

Regulation of Dihydroretinoid Metabolism

Studies of the dihydroretinoid pathway have led to the discovery of novel biologically active derivatives of vitamin A, such as all-trans-13,14-dihydroretinoic acid. We propose to study the levels of dihydroretinoids in relation to diabetic disease. Dihydroretinoid metabolism is studied in vivo in wild type mice and in various disease models. We showed that the expression of RetSat, hence dihydroretinoid metabolism, is altered by the metabolic/disease state of the animal. Most experiments use 6-12-week-old mice healthy and mouse models of diabetic disease, such as type I, NOD and type II, ob/ob, db/db, and diet induced obesity (DIO) mice. A comparison is made between the generation of various dihydroretinoid metabolites from stable labeled [11, 12-3H]all-trans-retinol in mouse models of diabetes and obesity. Animals are maintained on a control chow diet up to 1 h prior to oral gavage. The appropriate amount of all-trans-3,4-didehydroretinol as an internal standard is dissolved in vegetable oil and administered by oral gavage 3 h prior to analysis. Tissues from retinoid gavaged mice is homogenized in 137 mM NaCl, 2.7 mM KCl, and 10 mM sodium phosphate (pH 7.4) for 30 s using a Polytron homogenizer. In order to extract non-polar retinoids, the acid retinoids are deprotonated by adding NaOH to the ethanolic extract, and the nonpolar retinoids are extracted using 5 ml of hexane. The extraction is repeated, and the organic phases will be combined, dried under vacuum, resuspended in hexane, and examined by normal phase HPLC using a normal phase column (Beckman Ultrasphere Si 5µ, 4.6×250 mm). The elution condition is an isocratic solvent system of 10% ethyl acetate in hexane (v/v) for 25 min at a flow rate of 1.4 ml/min at 20° C. with detection at 325 and 290 nm for the detection of nonpolar retinoids and 13,14-dihydroretinoids, respectively. The aqueous phase can then be acidified with 12 N HCl, and polar retinoids are extracted with 5 ml of hexane. The extraction is repeated, and the organic phases of the polar retinoid extractions is combined, dried, resuspended in solvent composed of 80% CH3CN, 10 mM ammonium acetate, 1% acetic acid, and examined by reverse phase HPLC.

Analysis of polar retinoids from tissues is done by reverse phase HPLC using a narrowbore, 120-Å, 5-µm, 2.1×250 mm, Denali C18 column (Grace-Vydac, Hesperia, Calif.). The solvent system is composed of buffer A, 80% methanol, 20% 36 mM ammonium acetate (pH 4.7 adjusted with acetic acid), and buffer B, 100% methanol. The HPLC elution conditions are 0.3 ml/min, 100% buffer A for 40 min, 100% buffer B for 10 min, and 10 min equilibration in buffer A. The elution profiles of RA and DRA are monitored using an online diode array detector set at 350 and 290 nm, respectively. The peaks are identified based on their UV-visible spectra and/or coelution with synthetic or commercially available standards. The measured area of absorbance is converted to picomoles based on a calibration of the HPLC columns using a known amount of all-trans-13,14-dihydroretinol or all-trans-13,14-dihydroretinoic acid (synthetic standards). In the case of liver samples the extraction efficiency is usually 95% or better. Mass spectrometry analyses of synthesized retinoids and of natural retinoids purified by HPLC is performed using a Kratos profile HV-3 direct probe mass spectrometer. The rates of synthesis and breakdown of the bioactive dihydroretinoid are studied to identify their sites of origin and target tissues. These studies should greatly expand the knowledge of the physiological relevance of dihydroretinoids and form the basis for the development of effective pharmaceutical tools. Such studies should help us understand the kinetics of dihydroretinoid metabolism and allow us to design pharmacological applications for dihydroretinoid-based drugs.

From the above description of the invention, those skilled in the art will perceive improvements, changes and modifications. For example, it should be appreciated that a cell or population of cells, such as transgenic pancreatic β cells expressing a polynucleotide encoding all-trans-retinol:all-trans-13,14-dihydroretinol saturase, may be administered to a subject with a metabolic disease. Such improvements, changes and modifications within the skill of the art are intended to be covered by the appended claims. All references, publications, and patents cited herein are incorporated by reference in their entirety.

Having described the invention, we claim:

1. A method of treating obesity or an obesity related condition in a mammalian subject, the method comprising administering to the subject a therapeutically effective amount of a pharmaceutical composition comprising at least one all-trans-13,14-dihydroretinoid, all-trans-13,14-dihydroretinoid derivative, or all-trans-retinol: all-trans-13,14-dihydroretinol saturase, wherein the obesity or obesity related condition is associated with improved glucose tolerance, abnormal fasting response manifested by visceral fat retention, or decreased hepatic triglyceride levels.

2. The method of claim 1, the pharmaceutical composition being administered to at least one cell expressing G-protein-coupled receptor 40 (GPR40) and/or a polynucleotide encoding GPR40.

3. The method of claim 1, the pharmaceutical composition promoting lipolysis in the subject.

4. The method of claim 1, the pharmaceutical composition promoting hepatic uptake and esterification of free fatty acids.

5. The method of claim 1, the pharmaceutical composition comprising at least one of (R)-all-trans-13,14-dihydroretinol, (S)-all-trans-13,14-dihydroretinol, (R)-all-trans-13,14-dihydroretinoic acid, or (S)-all-trans-13,14-dihydroretinoic acid, or an ester thereof.

6. The method of claim 1, the pharmaceutical composition comprising at least 75% of (R)-all-trans-13,14-dihydroretinol, (R)-all-trans-13,14-dihydroretinoic acid, or an ester thereof.

7. The method of claim 1, the pharmaceutical composition comprising at least 75% of (S)-all-trans-13,14-dihydroretinol, (S)-all-trans-13,14-dihydroretinoic acid, or an ester thereof.

* * * * *